United States Patent
Rösch et al.

(10) Patent No.: US 10,508,127 B2
(45) Date of Patent: Dec. 17, 2019

(54) CONJUGATED BISPHOSPHONATES FOR THE DIAGNOSIS AND THERAPY OF BONE DISEASES

(71) Applicant: SCV GmbH, Zornheim (DE)

(72) Inventors: Frank Rösch, Mainz (DE); Marian Meckel, Munich (DE)

(73) Assignee: SCV GmbH, Zornheim (DE)

( * ) Notice: Subject to any disclaimer, the term of this patent is extended or adjusted under 35 U.S.C. 154(b) by 79 days.

(21) Appl. No.: 15/519,745

(22) PCT Filed: Oct. 16, 2015

(86) PCT No.: PCT/EP2015/002054
§ 371 (c)(1),
(2) Date: Apr. 17, 2017

(87) PCT Pub. No.: WO2016/058704
PCT Pub. Date: Apr. 21, 2016

(65) Prior Publication Data
US 2017/0327520 A1  Nov. 16, 2017

(30) Foreign Application Priority Data
Oct. 17, 2014 (DE) .................. 10 2014 115 154

(51) Int. Cl.
*C07F 9/6558* (2006.01)
*A61K 51/04* (2006.01)
*A61K 31/675* (2006.01)

(52) U.S. Cl.
CPC ........ *C07F 9/65583* (2013.01); *A61K 31/675* (2013.01); *A61K 51/0489* (2013.01)

(58) Field of Classification Search
CPC ............ A61K 51/0489; A61K 51/0497; A61K 31/675; C07F 9/65583
See application file for complete search history.

(56) References Cited

U.S. PATENT DOCUMENTS

2014/0271483 A1* 9/2014 Satchi-Fainaro ...... A61K 47/24
424/9.6

FOREIGN PATENT DOCUMENTS

EP      2468760 A1      6/2012
WO   WO-2002062398 A2   8/2002

OTHER PUBLICATIONS

Meckel et al. "In vivo comparison of DOTA based 68Ga-labelled bisphosphonates for bone imaging in non-tumour models," *Nuclear Medicine and Biology*, vol. 40, No. 6, Aug. 1, 2013, pp. 823-830.
Ogawa et al., "Preparation and evaluation of a radiogallium complex-conjugated bisphosphonate as a bone scintigraphy agent," *Nuclear Medicine and Biology*, Elsevier, NY, US, vol. 38, No. 5, Dec. 17, 2010, pp. 631-636.
Russell et al., "Mechanisms of action of bisphosphonates: similarities and differences and their potential influence on clinical efficacy," *Osteoporosis International*; With Other Metabolic Bone Diseases, Springer-Verlag, Lo, vol. 19, No. 6, Jan. 24, 2008, pp. 733-759.

* cited by examiner

*Primary Examiner* — Michael G. Hartley
*Assistant Examiner* — Leah H Schlientz
(74) *Attorney, Agent, or Firm* — Julie K. Staple; Dinsmore & Shohl LLP

(57) ABSTRACT

The invention relates to a compound V for complexing metallic isotopes, comprising a chelator X and one or more targeting vectors conjugated with the chelator X, said targeting vectors having the structure $-L_1-R_1-L_2-R_2-L_3-R_3$, wherein $R_3$ contains a bisphosphonate. A pharmaceutical consists of the compound V and a metallic isotope which is complexed with compound V.

$$X-L_1-C(=O)-NH-L_2-R_2-L_3-C(PO_3H_2)(PO_3H_2)-Z$$

Z = OH, H, $NH_2$ or Cl

20 Claims, 6 Drawing Sheets

CONJUGATED BISPHOSPHONATES FOR THE DIAGNOSIS AND THERAPY OF BONE DISEASES

CROSS REFERENCE TO RELATED APPLICATIONS

This application claims priority to PCT/EP2015/002054 filed Oct. 16, 2015 which claims priority to 102014115154.2 (DE) filed Oct. 17, 2014.

The present invention relates to a compound V for complexing metallic isotopes, comprising a chelator X and one or more targeting vectors conjugated with the chelator X, said targeting vectors having the structure -$L_1$-$R_1$-$L_2$-$R_2$-$L_3$-$R_3$, wherein $R_3$ contains a bisphosphonate. Furthermore, the invention relates to a pharmaceutical that consists of the compound V and a metallic isotope which is complexed with compound V, as well as a method to produce the pharmaceutical.

Bisphosphonates (BP) are a substance group for the treatment of bone and calcium metabolic diseases. Among these are Paget's disease, osteoporosis, and the conventional systemic treatment of bone tumors. Bisphosphonates are characterized by a pronounced selectiveness in their accumulation of mineral calcium phosphate in the organism. They trigger multiple effects in the target tissue. On the one hand, they inhibit the mineralization of the bone substance; on the other hand, they inhibit bone degradation. Their effect is based on, among other things, the inhibition of farnesyl pyrophosphate synthesis (FPPS), an enzyme in the HMG-CoA reductase (mevalonate) path. The production of farnesyl—an important molecule for anchoring signal proteins to the cell membrane in the cell (FPPS), is inhibited via the inhibition of the enzyme.

Apoptosis in the cell is initiated as a result. Such bisphosphonate derivatives thereby already have a therapy-relevant function, even at the level of an individual cell.

Due to the selective accumulation of bisphosphonates at the bone surface, the apoptotic effect relates especially to the osteogenic cells, primarily hereby the osteoclasts, which take up the bisphosphonates to a greater extent due to the demineralization of the bone matrix. An antiresorptive effect is achieved via the reduction of the osteoclast activity.

The following bisphosphonates are clinically relevant today: clodronate, alendronate, etidronate, ibandronate, risedronate and zoledronate. The following abbreviations are used herein:

ZOL=zolendronate.
PAM=pamidronate.

With the conjugates described herein, these abbreviations are written in superscript after the names or the abbreviation of the chelator X: for example, DOTA$^{PAM}$ designates the pamidronate-DOTA conjugate.

Within the bisphosphonate compound class, a differentiation is made between α-H bisphosphonates, α-hydroxy bisphosphonates, nitrogen-containing bisphosphonates (N-BP) and heterocyclic nitrogen-containing bisphosphonates. These differ significantly in their bonding effectiveness to bone, their pharmacokinetics, and their inhibition potential of the FPPS due to different structure-effect relationships.

The kinetic bonding affinity to mineral bone substance or to artificial hydroxyapatite (HA) increases with the following order of the compounds: clodronate<etidronate<risedronate<ibandronate<alendronate<pamidronate<zoledronate, and in the sequence of α-H bisphosphonates to α-hydroxy bisphosphonates. The additional OH group represents a coordination point for bonding to HA. An additional important factor that determines the affinity to HA is the nitrogen atom in the $C_{3-4}$ position at the geminal bisphosphonates of the N bisphosphonate and heterocyclic N bisphosphonates. This likewise serves as an additional donor location to HA, but also has a decisive influence on the zeta potential of the bisphosphonates given a physiological pH value. Bisphosphonates having a positively charged side chain (such as alendronate, pamidronate and zoledronate) show higher bonding capacities to HA (R. G. G. Russell, N. B. Watts, F. H. Ebetino, M. J. Rogers, Mechanisms of action of bisphosphonates: similarities and differences and their potential influence on clinical efficacy, Osteoporose Int. 2008; 19: 733-759).

Radioactive tracers based on compounds that exhibit a bonding capacity to the different functionalities of HA have been routinely used for a long time for diagnostic and also for therapeutic purposes.

Radioactively marked bisphosphonates such as [$^{99m}$Tc] MDP (methanediphosphonic acid) or [$^{99m}$Tc]HMDP (hydroxymethanediphosphonic acid) are used in bone scintigraphy of metabolic bone diseases and bone tumors. Relative to bone scintigraphy or SPECT (Single Photon Computed Tomography), however, PET (Positron Emission Tomography) with [$^{18}$F]NaF represents a markedly more sensitive method for detection of bone tumors. Radio-marked bisphosphonates as PET tracers are not commercially established (E. Even-Sapir, U. Metser, G. Lievshitz, H. Lerman, I. Leibovitch, The Detection of Bone Metastases in Patients with High-Risk Prostate Cancer: $^{99m}$Tc-MDP Planar Bone Scintigraphy, Single- and Multi-Field-of-View SPECT, $^{18}$F-Fluoride PET, and $^{18}$F-Fluoride PET/CT, J. Nucl. Med. 2006; 47: 287-297).

Palliative pain therapy of bone tumors represents an additional field of use of radiometals. The radioisotopes of metals of the second main group, such as $^{89}$Sr(II) and $^{223}$Ra(II), are especially used here. These calcium analogues are stored with high biological half-life, similar to calcium, in the mineralization of the bone. $^{223}$Ra(II) was allowed in 2013 as a palliative endoradiotherapeutic for treatment of bone tumors. However, the elimination of the radioactive substance via the intestine proves to be a problem with these calcium mimetics (see FIG. 1: Comparison of [$^{99m}$Tc]MDP and $^{223}$RaCl$_2$ on day 1, 2 and day 6 after the injection, from O. Sartor, P. Hoskin, Ø. S. Bruland, Targeted radio-nuclide therapy of skeletal metastases, Cancer Treatment Reviews, 2013; 39: 18-26).

Trivalent metallic radionuclides such as $^{153}$Sm(III), $^{177}$Lu (III) and $^{90}$Y(III) must be injected with the aid of a weak chelator such as citrate, EDTMP (ethylene diamine tetra [methylene phosphonic acid]) or HEDTA ([hydroxyethyl]-ethylene diamine triacetic acid) in order to avoid complex dissociation and hepatic accumulation. Stabilizations of the trivalent radiolanthanides in the form of macrocyclic chelators have not been established. This is inasmuch noteworthy since, for example, β-emitting $^{177}$Lu is also commercially promising for therapeutic approaches for bone tumors due to its nuclear characteristics (half-life, ratio, and energy of the β-particles), its commercial availability and the carrier-free concentration.

The positron emitter $^{68}$Ga is extraordinarily relevant in the field of quantitative imaging, both for reasons of its generator-based availability and due to its nuclear and chemical characteristics. Solely as a trivalent cation, it is not sufficiently selective with regard to accumulation at bone tumors. Typically, $^{68}$Ga-complexes are required in which the ligands have phosphonate profiles that should impart an affinity to HA and an advantageous pharmacology in the other organs.

In the context of compounds with bone affinity, EDTMP having $^{68}$Ga(III) was evaluated, but shows only an insufficient accumulation in the target tissue and consequently is only insufficiently suitable as a diagnostic agent (J. Goyal, E. S. Antonarakis, Bone-targeting radiopharmaceuticals for the treatment of prostate cancer with bone metastases, Cancer Letters, 2012; 323: 135-146; O. Sartor, P. Hoskin, Ø. S. Bruland, Targeted radio-nuclide therapy of skeletal metastases, Cancer Treatment Reviews, 2013; 39: 18-26; M. Mitterhauser, S. Toegela, W. Wadsak, R. Klugerg, H. Viernstein, R. Dudczaka, K. Kletter, Pre vivo, ex vivo and in vivo evaluations of [$^{68}$Ga]EDTMP, Nuclear Medicine and Biology, 2007; 34: 391-397).

Macrocyclic ligands are the current focus of research, primarily DOTA (1,4,7,10-tetraazacyclododecane-1,4,7,10-tetraacetic acid), DOTAM (1,4,7,10-tetrakis(carbamoylmethyl)-1,4,7,10-tetraazacyclododecane) or NOTA (1,4,7-triazacyclononane-1,4,7-triacetic acid) as conjugated bisphosphonates. Due to their macrocyclic bifunctional chelator, these are suitable for stable complexing of the most varied radiometals, for example $^{68}$Ga(III) and the therapy nuclide $^{177}$Lu(III). Exclusively α-H bisphosphonates and α-hydroxy bisphosphonates are found among the DOTA bisphosphonates or NOTA bisphosphonates described in the technical literature and patent specifications, but no N-heteroaromatic compounds (M. Meckel, M. Fellner, N. Thieme, R. Bergmann, V. Kubicek, F. Rösch, In vivo comparison of DOTA based $^{68}$Ga-labelled bisphosphonates for bone imaging in non-tumour models, Nucl. Med. Biol., 2013; 40: 823-830; K. Ogawa, K. Takai, H. Kanbara, T. Kiwada, Y. Kitamura, K. Shiba, A. Odani, Preparation and evaluation of a radiogallium complex-conjugated bisphosphonate as a bone scintigraphy agent, Nuc. Med. Biol., 2011; 38: 631-636; US 2012/0148492 A1, Jun. 14, 2012, Bisphosphonic acid derivative and compound thereof labeled with radioactive metal nuclide, Hiroyuki Dozono, Fujifilm RI Pharma Co. Ltd., Tokyo, Japan).

The N-containing α-H bisphosphonates or α-hydroxy bisphosphonates that are known in the prior art use DOTA or NOTA as a chelator, wherein the geminal bisphosphonates are conjugated via an amide bond to the nitrogen atom in the $C_{3-4}$ position of the chelator. However, the known conjugates of N-containing α-H bisphosphonates or α-hydroxy bisphosphonates have a strongly reduced affinity to bone substance in comparison to geminal bisphosphonate. It is assumed that the derivation of the respective geminal bisphosphonate significantly reduces its affinity. Other N-heteroaromatic α-hydroxy bisphosphonates (for example zoledronate) which exhibit a high affinity to bone substances previously could not be conjugated with a bifunctional chelator.

The invention has the object of providing a pharmaceutical with an accumulation at bones, in particular at bone tumors, that is increased in comparison to the prior art. A better accumulation ratio for bone-to-blood and bone-to-soft tissue, a greater binding yield to bone tumors, and an efficient renal excretion of unbound pharmaceutical should hereby be achieved. Depending on the selection of the radionuclide, the bisphosphonate derivatives according to the invention should be usable for molecular imaging, in particular as a PET diagnostic agent, and as an endoradiotherapeutic agent.

This object is achieved via a compound V comprising a chelator X and one or more targeting vectors (TV) conjugated with the chelator X, said targeting vectors having the structure -$L_1$-$R_1$-$L_2$-$R_2$-$L_3$-$R_3$, wherein $L_1$ is selected from the group comprising amide, phosphinate, alkyl, triazole, thiourea, ethylene, maleimide, —(CH$_2$)$_k$— and —(CH$_2$CH$_2$O)$_k$—, with k=1, 2, 3, 4, 5, 6, 7, 8, 9 or 10, $L_2$ is selected from —(CH$_2$)$_m$— and —(CH$_2$CH$_2$O)$_m$—, with m=1, 2, 3, 4, 5, 6, 7, 8, 9 or 10, and $L_3$ is selected from —(CH$_2$)$_n$— and —(CH$_2$CH$_2$O)$_n$—, with n=1, 2, 3, 4, 5, 6, 7, 8, 9 or 10, and

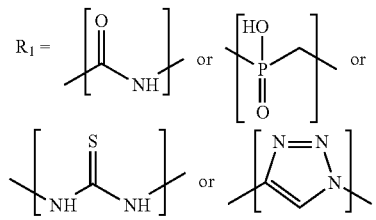

$R_2$ is selected from the group comprising a substituent group of a:
furan, azole, oxazole, thiophen, thiazole, azine, oxazine, thiazine, naphthalene, quinoline, chromene or thiochromene;

and

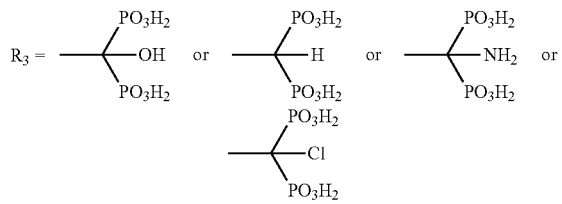

The term "chelator" or the designation "X" herein generally designates a compound that is capable of complexing a metal ion. Preferred chelators are cyclic compounds that are optionally provided with one or more side chains. Such cyclic compounds having one or more side chain(s) are also designated as "macrocyclic ligands" or "macrocyclic chelators". One example of a macrocyclic chelator having four side chains is DOTA: it is comprised of the 12-element macrocycle 1,4,7,10-tetraazacyclododecane, which is substituted with acetic acid substituents at the four nitrogen atoms of the macrocycle, thus the positions 1,4,7 and 10 of the macrocycle: thus 1,4,7,10-tetraazacyclododecane-1,4,7,10-tetraacetic acid.

The term "derivative" referring to a chelator X, designates a compound that differs from this chelator X in that at least one group of the chelator X is replaced by a different group. With regard to a derivative of a chelator, it may be synonymously expressed that the derivative is "derived" from the chelator. With regard to the chelator X, such compounds are designated herein as its derivative or their derivatives. If the chelator X is a macrocyclic ligand, the derivative differs from the chelator either (a) in that at least one group that is a component of the macrocycle is replaced by a different group (for example, a methylene group may be replaced by an ethylene group, or the reverse) and/or (b) in that at least one group that is a side chain or a component of a side chain is replaced by a different group (for example, an acetic acid group may be replaced by an acetic acid amide group, or the reverse). Derivatives having a difference of type (b) are preferred. Additionally preferred among these are derivatives having a difference of type (b), but without a difference of type (a). An example of a derivative of the chelator DOTA is the compound DOTAM, in which all four acetic acid group side chains of DOTA are replaced with acetic acid amide groups. The derivative is itself preferably a chelator, meaning a compound that is capable of complexing a metal ion.

Advantageous embodiments of the invention are characterized in that:

the chelator X is selected from the group comprising EDTA (ethylenediamine-tetraacetate), EDTMP (diethylenetriamine penta(methylene phosphonic acid)), DTPA (diethylenetriamine pentaacetic acid) and its derivatives, DOTA (1,4,7,10-tetraazacyclododecane-1,4,7,10-tetraacetic acid), DOTAGA (dodeca-1-glutaric acid-1,4,7,10-tetraamine-triacetic acid), DOTAM (1,4,7,10-tetrakis(carbamoylmethyl)-1,4,7,10-tetraazacyclododecane) and other DOTA derivatives, TRITA (trideca-1,4,7,10-tetraamine tetraacetic acid), TETA (tetradeca-1,4,8,11-tetraamine-tetraacetic acid) and its derivatives, NOTA (nona-1,4,7-triamine-triacetic acid) and its derivatives, for example NOTAGA (1,4,7-triazacyclononane,1-glutaric acid,4,7-acetic acid), NOPO (1,4,7-triazacyclononane-1,4-bis[methylene(hydroxymethyl)hypophosphorous acid]-7-[methylene(2-carboxyethyl)hypophosphorous acid]), PEPA (pentadeca-1,4,7,10,13-pentaamine pentaacetic acid), HEHA (hexadeca-1,4,7,10,13,16-hexaamine hexaacetic acid) and its derivatives, HBED (hydroxybenzyl-ethylenediamine) and its derivatives, DEDPA and its derivatives, such as $H_2$DEDPA (1,2-[{6-(carboxylate-)pyridine-2-yl}methylamine]ethane), DFO (deferoxamine) and its derivatives, Deferiprone, CP256 (4-acetylamino-4-{2-[(3-hydroxy-1,6-dimethyl-4-oxo-1,4-dihydro-pyridine-2-ylmethyl)-carbamoyl]-ethyl}-heptane diacid bis-[(3-hydroxy-1,6-dimethyl-4-oxo-1,4-dihydro-pyridine-2-ylmethyl)-amide]) and its derivatives, such as YM103; TRAP (triazacyclononane-hypophosphorous acid), TEAP (tetraazycyclodecane-hypophosphorous acid) and its derivatives, AAZTA (6 amino-6-methylperhydro-1,4-diazepine-N,N,N',N'-tetraacetic acid) and derivatives such as DATA; SarAr (1-N-(4-aminobenzyl)-3,6,10,13,16,19-hexaazabicyclo[6.6.6]-eicosane-1,8-diamine) and salts thereof;

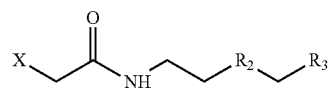

(I)

the compound V has a structure according to Formula I wherein X designates the chelator; and/or
the compound V has a structure according to Formula II,

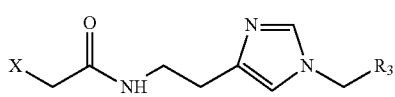

(II)

wherein X designates the chelator.

The invention additionally has the object of providing a pharmaceutical for the treatment of bone diseases. This object is achieved via a pharmaceutical that comprises the compound V described in the preceding and a metallic isotope M complexed with the compound V. The metallic isotope M is preferably selected from the group comprising $^{44}$Sc, $^{47}$Sc, $^{55}$Co, $^{62}$Cu, $^{64}$Cu, $^{67}$Cu, $^{66}$Ga, $^{67}$Ga, $^{68}$Ga, $^{89}$Zr, $^{86}$Y, $^{90}$Y, $^{90}$Nb, $^{99m}$Tc, $^{111}$In, $^{135}$Sm, $^{159}$Gd, $^{149}$Tb, $^{160}$Tb, $^{161}$Tb, $^{165}$Er, $^{166}$Dy, $^{166}$Ho, $^{175}$Yb, $^{177}$Lu, $^{186}$Re, $^{188}$Re, $^{213}$Bi and $^{225}$Ac. $^{66}$Ga, $^{67}$Ga, $^{68}$Ga and $^{177}$Lu are especially preferred.

Especially preferred in this invention are those combinations made up of a preferred metallic isotope and/or a preferred chelator X and/or a preferred compound V, having a preferred bisphosphonate.

An additional object of the present invention is to provide a method to produce a pharmaceutical made up of the compound V and a metallic isotope M.

This object is achieved via a method which includes the following steps:

(a) providing a solution S containing the compound V according to any of the claims 1 to 4;
(b) providing a metallic isotope M, such as $^{68}$Ga(III); and
(c) ligating the metallic isotope M with the compound V to form a complex MV of the metallic isotope M with the compound V in a solution F.

Expedient embodiments of the method according to the invention are characterized in that:

in step (b) the metallic isotope M is provided in a solution;
in step (b) a radionuclide generator with a mother nuclide and a metallic isotope M generated via decay of the mother nuclide is provided, and in step (c) the metallic isotope M is separated from the mother nuclide with the solution S;
in step (b), the metallic isotope M is contained in an ion exchanger, and in step (c), the metallic isotope M is eluted from the ion exchanger with the solution S;
in step (b), the metallic isotope M is contained in an ion exchanger, and in step (c), the metallic isotope M is eluted from the ion exchanger with a solvent E in order to obtain the solution ME containing the metallic isotope M, and the solution ME is mixed with the solution S in order to obtain the solution F with the complex MV;
in step (c), before the elution of the metallic isotope M, the ion exchanger is flushed with one or more solvents in order to remove contaminants;
the ion exchanger is a cation exchanger;
the ion exchanger contains as an active component sulfonated poly(styrene-co-divinylbenzene) resin, wherein the poly(styrene-co-divinylbenzene) resin contains divinylbenzene in a quantity of 2 to 20 mol % based on 100 mol % styrene and divinylbenzene monomer units;
following step (c), the solution F is filtered and/or neutralized;
step (c) is concluded within 6 s to 3 min, within 6 s to 2 min, or preferably within 6 s to 1 min;
step (c) is implemented at a temperature of 10 to 95° C., of 10 to 90° C., of 10 to 40° C. or preferably of 10 to 30° C.;
in step (b) a radionuclide generator is used, wherein the radionuclide generator is a mother nuclide adsorbed at a chromatographic column, e.g., comprises $^{68}$Ge, and a daughter nuclide formed via decay of the mother nuclide, e.g., $^{68}$Ga, is eluted from the chromatographic column; and/or
in step (b) a radionuclide generator is used, wherein the radionuclide generator is a solution having a mother nuclide, e.g., comprises $^{90}$Sr, and a daughter nuclide generated via decay of the mother nuclide, e.g., $^{90}$Y, is eluted from the solution.

The compound V comprises a chelator X and one or more targeting vectors conjugated with the chelator X, said targeting vectors having the structure -$L_1$-$R_1$-$L_2$-$R_2$-$L_3$-$R_3$. The compound V especially has the one of the following structures:

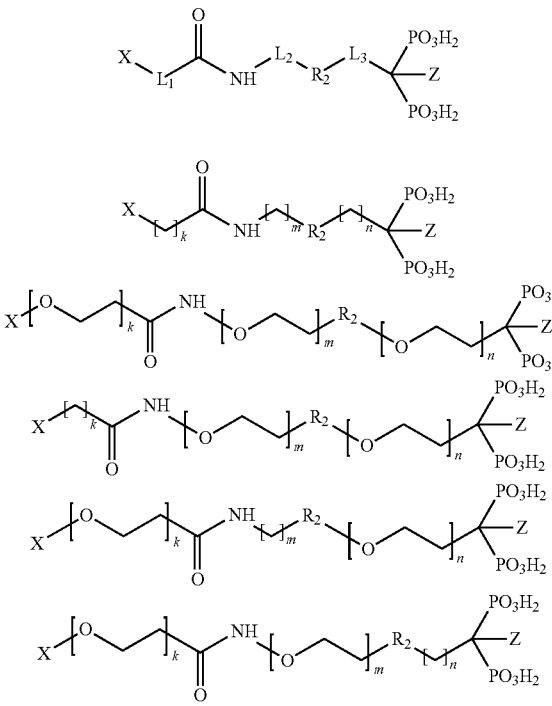

with k=1, 2, 3, 4, 5, 6, 7, 8, 9 or 10;
m=1, 2, 3, 4, 5, 6, 7, 8, 9 or 10;
n=1, 2, 3, 4, 5, 6, 7, 8, 9 or 10; and
Z=OH, H, $NH_2$ or Cl.

$R_2$ is preferably selected from the group comprising substituent groups of the molecules:

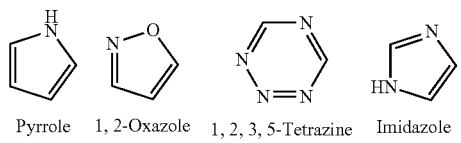

Pyrrole    1,2-Oxazole    1,2,3,5-Tetrazine    Imidazole

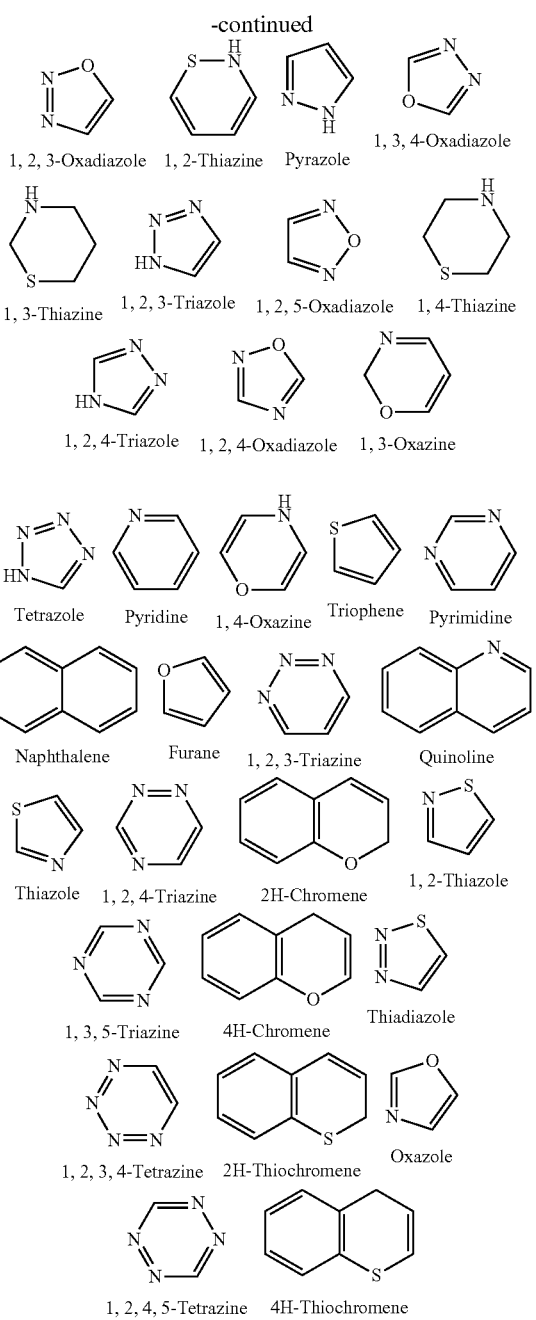

and isomers of the preceding molecules.

Accordingly, the compound V according to the invention has a structure identical or analogous to the compounds shown in the following, wherein the molecule from which the group $R_2$ derives is respectively indicated:

| Molecule from which $R_2$ is derived | Compound V | Structure No. |
|---|---|---|
| Pyrrole | | (IV) |

| Molecule from which R₂ is derived | Compound V | Structure No. |
|---|---|---|
| Imidazole | ![structure with imidazole ring] | (V) |
| Pyrazole | ![structure with pyrazole ring] | (VI) |
| 1,2,3-Triazole | ![structure with 1,2,3-triazole ring] | (VII) |
| 1,2,4-Triazole | ![structure with 1,2,4-triazole ring] | (VIII) |
| Tetrazole | ![structure with tetrazole ring] | (IX) |
| Thiophene | ![structure with thiophene ring] | (X) |
| Furan | ![structure with furan ring] | (XI) |
| Thiazole | ![structure with thiazole ring] | (XII) |
| 1,2-Thiazole | ![structure with 1,2-thiazole ring] | (XIII) |
| Thiadiazole | ![structure with thiadiazole ring] | (XIV) |

-continued

| Molecule from which R₂ is derived | Compound V | Structure No. |
|---|---|---|
| Oxazole | X-CH₂-C(O)-NH-CH₂CH₂-[oxazole]-C(PO₃H₂)(Z)(PO₃H₂) | (XV) |
| 1,2-Oxazole | X-CH₂-C(O)-NH-CH₂CH₂-[isoxazole]-C(PO₃H₂)(Z)(PO₃H₂) | (XVI) |
| 1,2,3-Oxadiazole | X-CH₂-C(O)-NH-CH₂CH₂-[1,2,3-oxadiazole]-C(PO₃H₂)(Z)(PO₃H₂) | (XVII) |
| 1,3,4-Oxadiazole | X-CH₂-C(O)-NH-CH₂CH₂-[1,3,4-oxadiazole]-C(PO₃H₂)(Z)(PO₃H₂) | (XVIII) |
| 1,2,5-Oxadiazole | X-CH₂-C(O)-NH-CH₂CH₂-[1,2,5-oxadiazole]-C(PO₃H₂)(Z)(PO₃H₂) | (XIX) |
| 1,2,4-Oxadiazole | X-CH₂-C(O)-NH-CH₂-[1,2,4-oxadiazole]-C(PO₃H₂)(Z)(PO₃H₂) | (XX) |
| Pyridine | X-CH₂-C(O)-NH-CH₂-[pyridine]-C(PO₃H₂)(Z)(PO₃H₂) | (XXI) |
| Pyrimidine | X-CH₂-C(O)-NH-CH₂-[pyrimidine]-C(PO₃H₂)(Z)(PO₃H₂) | (XXII) |
| 1,2,3-Triazine | X-CH₂-C(O)-NH-CH₂-[1,2,3-triazine]-C(PO₃H₂)(Z)(PO₃H₂) | (XXIII) |
| 1,2,4-Triazine | X-CH₂-C(O)-NH-CH₂-[1,2,4-triazine]-C(PO₃H₂)(Z)(PO₃H₂) | (XXIV) |
| 1,3,5-Triazine | X-CH₂-C(O)-NH-CH₂CH₂-[1,3,5-triazine]-C(PO₃H₂)(Z)(PO₃H₂) | (XXV) |
| 1,2,3,4-Tetrazine | X-CH₂-C(O)-NH-CH₂-[1,2,3,4-tetrazine]-C(PO₃H₂)(Z)(PO₃H₂) | (XXVI) |

-continued

| Molecule from which $R_2$ is derived | Compound V | Structure No. |
|---|---|---|
| 1,2,4,5-Tetrazine | | (XXVII) |
| 1,2,3,5-Tetrazine | | (XXVIII) |
| 1,2-Thiazine | | (XXIX) |
| 1,3-Thiazine | | (XXX) |
| 1,4-Thiazine | | (XXXI) |
| 1,3-Oxazine | | (XXXII) |
| 1,4-Oxazine | | (XXXIII) |
| Napthalene | | (XXXIV) |
| Quinoline | | (XXXV) |
| 2H-Chromene | | (XXXVI) |
| 4H-Chromene | | (XXXVII) |

| Molecule from which R₂ is derived | Compound V | Structure No. |
|---|---|---|
| 2H-Thiochromene | (structure) | (XXXVIII) |
| 4H-Thiochromene | (structure) | (XXXIX) |

In some of the compounds or structural formulas according to the invention that are shown in the preceding, the group $R_2$ is bordered by a dashed line that represents a Markush shading and indicates that any of the possible bonding locations of the group $R_2$ is used for the bond between $R_2$ and the group $R_3$ or -$L_3$-$R_3$ (meaning the bisphosphonate), as well as for the bond between $R_2$ and the group $R_1$ or —$R_1$-$L_2$-. The groups —$R_1$-$L_2$- and/or -$L_3$-$R_3$ especially may also be bound via a nitrogen atom of the NH substituent of the group $R_2$, wherein the bond replaces the hydrogen atom of the NH substituent.

In the preceding structural formulas:

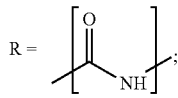

$L_1$=—(CH$_2$)$_k$— with k=1;
$L_2$=—(CH$_2$)$_m$— with m=2;
$L_3$=—(CH$_2$)$_n$— with n=1; and
Z=OH, H, NH$_2$ or Cl.

Within the scope of the invention, compounds are additionally provided in which

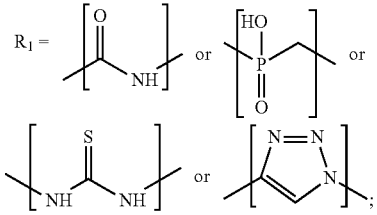

$L_1$ is selected from the group comprising an amide, phosphinate, alkyl, triazole, thiourea, ethylene, maleimide substituent, and —(CH$_2$)$_k$— or —(CH$_2$CH$_2$O)$_k$—, with k=1, 2, 3, 4, 5, 6, 7, 8, 9 or 10;

$L_2$=—(CH$_2$)$_m$— or —(CH$_2$CH$_2$O)m-, with m=1, 2, 3, 4, 5, 6, 7, 8, 9 or 10, and/or $L_3$=—(CH$_2$)$_n$— or —(CH$_2$CH$_2$O)$_n$—, with n=1, 2, 3, 4, 5, 6, 7, 8, 9 or 10.

The basic structure of some of the chelators X according to the invention is shown in the following.

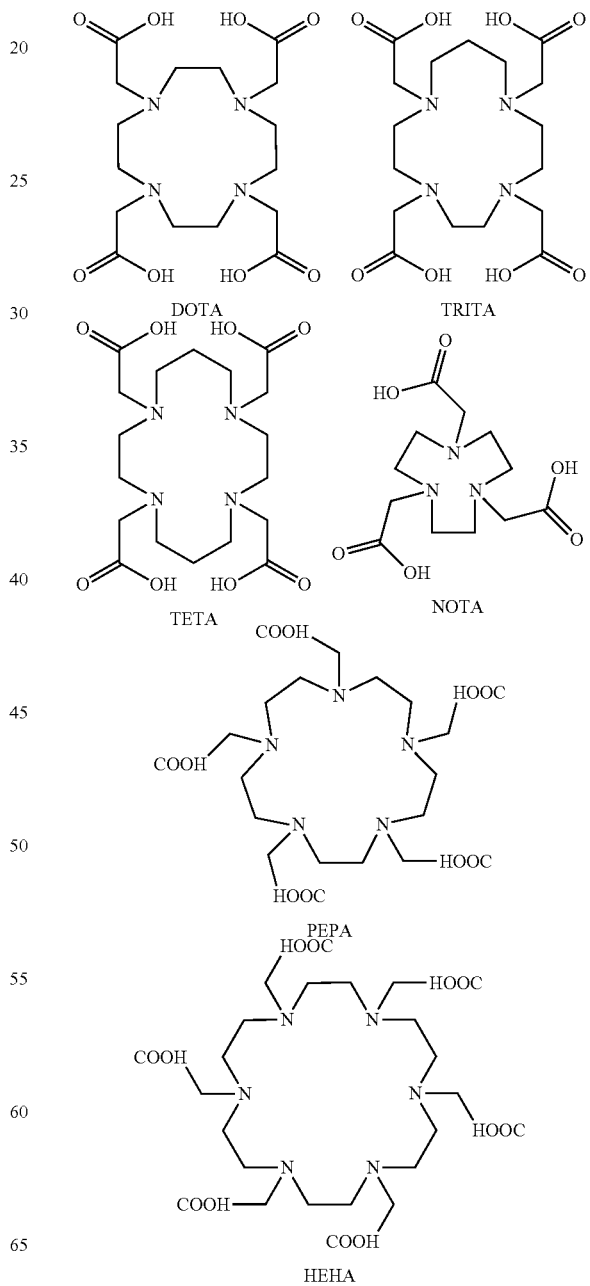

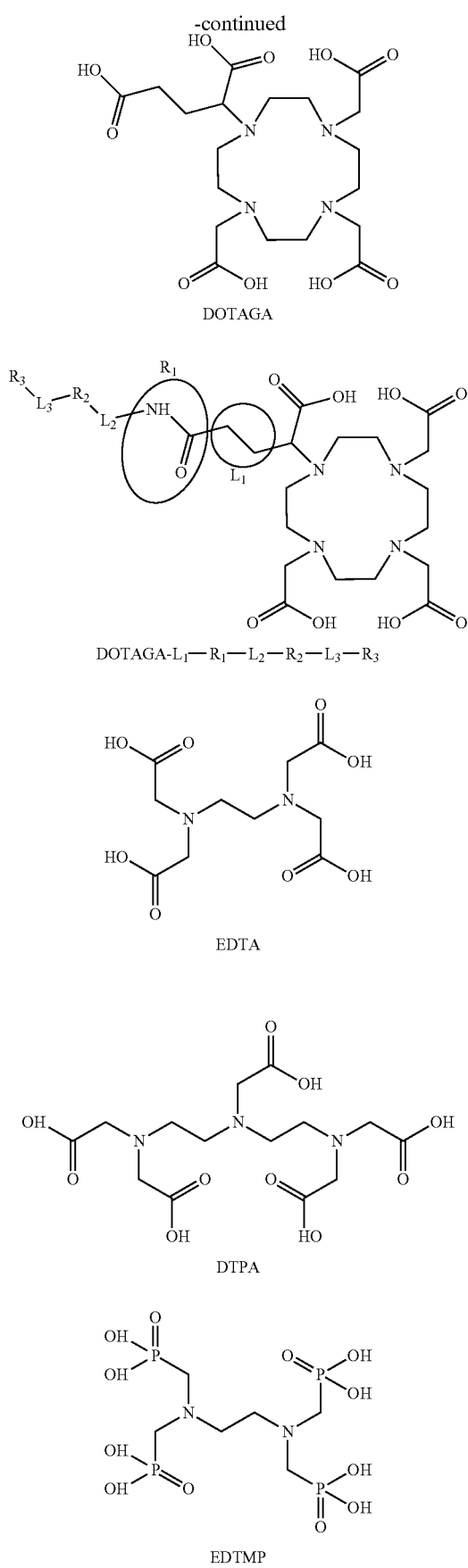
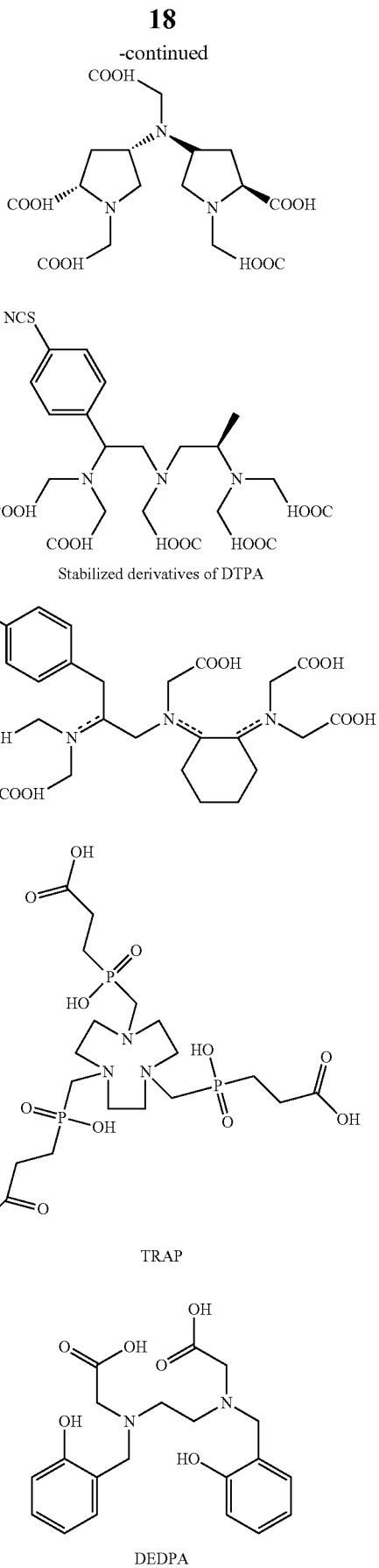

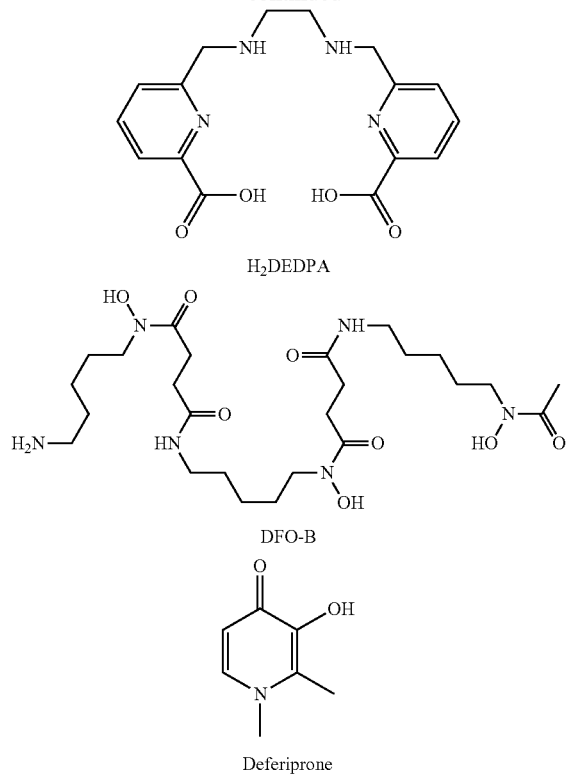

H₂DEDPA

DFO-B

Deferiprone

CP256

YM103

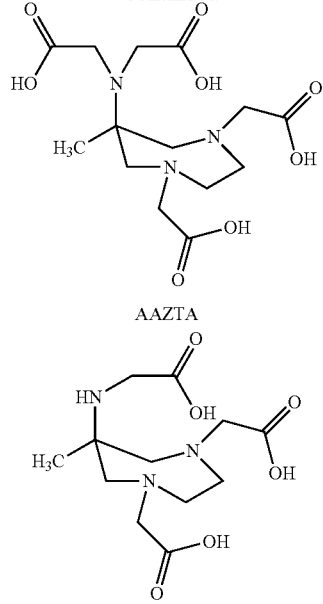

AAZTA 2,2'-{6-[(carboxymethyl)amino]-
6-methyl-1,4-diazepan-1,4-diyl}
diacetic acid A compound V that is especially preferred according to the invention is DOTA$^{ZOL}$, having the structural formula III

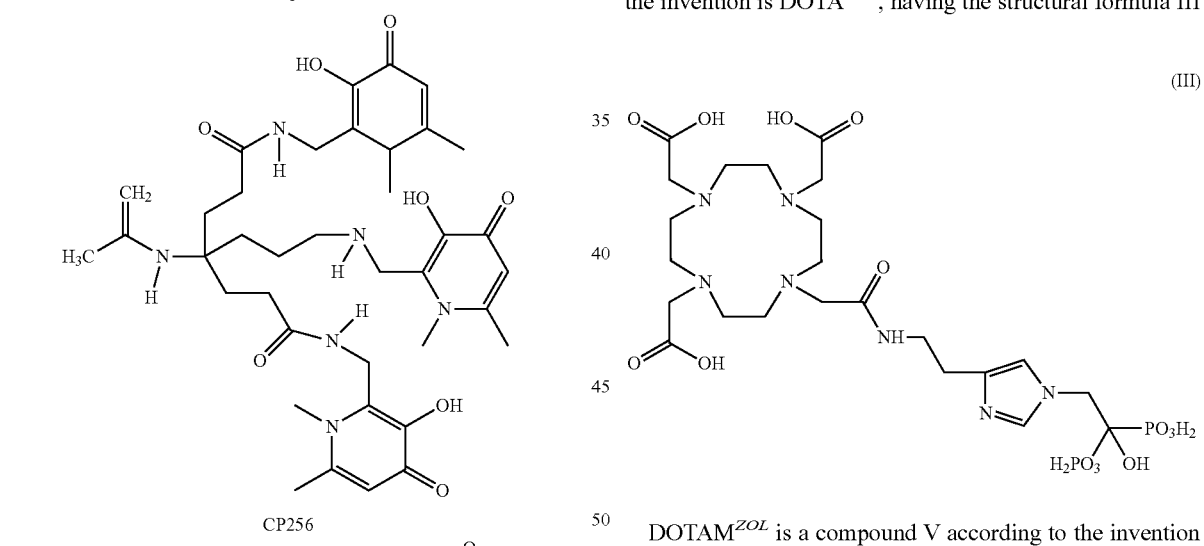

(III)

DOTAM$^{ZOL}$ is a compound V according to the invention that is likewise especially preferred.

Pharmaceuticals of the [M]DOTA$^{ZOL}$ type that are based on DOTA$^{ZOL}$, e.g., [$^{68}$Ga]DOTA$^{ZOL}$ and [$^{177}$Lu]DOTA$^{ZOL}$, as well as all derivatives derived from these (for example, DOTAM-based derivatives), can be efficiently produced and are stable chemically and under physiological conditions. In the preceding structural formulas, the complexing of the metallic isotope M is symbolized by square brackets.

This invention also relates to devices for producing a radiopharmaceutical.

FIG. 3 schematically shows a first device 1 for producing a radiopharmaceutical made up of the compound V according to the invention and a metallic radioisotope M which is preferably selected from $^{66}$Ga, $^{67}$Ga and $^{68}$Ga. Device 1 comprises a radionuclide generator 10 having a chromatographic column 12 at which a metallic mother nuclide such as $^{68}$Ge is adsorbed, and an elution device 11 for eluting a daughter nuclide M such as $^{68}$Ga, that is generated via decay of the mother nuclide, from the chromatographic column 12 with a suitable solvent. The elution device 11 comprises, for example, a recipient container for the solvent, and a pump. The various components of device 1 are connected with one another via fluid lines that are designated through FIG. 3 with the reference character 9. The outlet of the chromatographic column 12 is connected via a fluid line and a first multiple way valve 13 with the intake of an ion exchanger 14. The ion exchanger 14 preferably comprises sulfonated poly(styrene-co-divinylbenzene) resin as an active component, wherein the poly(styrene-co-divinylbenzene) resin comprises divinylbenzene in a quantity of 2 to 20 mol % based on 100 mol % styrene and divinylbenzene monomer units. The daughter nuclide M that is eluted from the chromatographic column 12 is adsorbed at the ion exchanger 14, whereas the mother nuclide that is likewise eluted is not adsorbed and is practically entirely directed via a second multiple-way valve 15 into a capture vessel 16.

The device 1 preferably comprises additional elution devices 21, 22, 23 that are connected with the intake of the ion exchanger 14 via fluid lines and the first multiple way valve 13. The elution devices 21, 22, 23 serve to purify the ion exchanger 14 or the daughter nuclide M adsorbed at the ion exchanger 14. In particular, residues that originate from the radionuclide generator 10, such as the mother nuclide, $Fe^{III}$, $Zn^{II}$ and $Ti^{IV}$, are removed by means of the elution devices 21, 22, 23. The one or more eluates or solvents that leave the ion exchanger 14 are likewise directed via the second multiple way valve 15 into the capture vessel 16.

An additional elution device 30 that is connected with the intake of the ion exchanger 14 via a fluid line and the first multiple way valve 13 is used to elute the purified daughter nuclide M from the ion exchanger 14. The eluate with the daughter nuclide M is directed via the second multiple way valve 15 into a reaction vessel 17. The reaction vessel 17 is preferably equipped with an electric heating device 17A. A solution containing the compound V according to the invention is directed from a recipient container 40 into the reaction vessel 17, whereby the complexing of the daughter nuclide M with the compound V is initiated. After conclusion of the complexing, the radioactively marked compound VM (meaning the radiopharmaceutical comprised of the compound V and the ligated daughter nuclide M) is directed across an optional filter 18 into a product vessel 19 where, if applicable, it is neutralized with a solution supplied from a recipient container 50.

FIG. 4 shows a second device 2 for producing a radiopharmaceutical made up of the compound V according to the invention and a metallic radioisotope M which is preferably selected from $^{66}$Ga, $^{67}$Ga and $^{68}$Ga. In FIG. 4, reference characters coinciding with FIG. 3 designate components with the same function. The second device 2 differs from the device 1 in that a solution containing the compound V according to the invention is connected from an elution device 43, via a fluid line and a multiple way valve 13, with the intake of an ion exchanger 14. The solution with the compound V is supplied directly to the ion exchanger 14, wherein the daughter nuclide M is simultaneously eluted and complexed. From the ion exchanger 14, the eluate with the compound V according to the invention and the metallic radioisotope M is directed into the product vessel 19 via the multiple way valve 15 and an optional filter 18. In instances in which the compound V according to the invention efficiently and stably complexes the daughter nuclide M, the radiopharmaceutical may be produced quickly and effectively by means of the device 2.

FIGS. 3 and 4 show specific devices with a radionuclide generator and an ion exchanger. However, a separate ion exchanger is not always required. Rather, for numerous applications it is appropriate to use the ion exchanger as an adsorber in the radionuclide generator.

In additional application instances or embodiments, neither a radionuclide generator nor an ion exchanger is required. In these application instances or embodiments, the metallic isotope or metallic radioisotope is provided in a solution.

Medical Uses and Other Uses Related to these

The present invention also relates to the use of a compound V according to the invention as a labelling precursor for the production of a medicine or pharmaceutical. The invention also relates to the use of a pharmaceutical of such a pharmaceutical in an imaging process by means of positron emission tomography or single photon emission computer tomography. The pharmaceutical according to the invention is suitable for use in a treatment or therapy process. It is especially suitable for use in a method for treatment of bone diseases and bone tumors. Such a method for the treatment of bone diseases and bone tumors is therefore according to the invention. Such methods in particular include methods for use of the pharmaceutical in the treatment of diseases of non-manifested bone metastases. These methods preferably include the accumulation in the tumor cells in order to inhibit farnesyl pyrophosphate synthesis (FPPS). Other medical methods and uses of the pharmaceutical according to the invention include the imaging of pharmacokinetic processes (such as heart diseases) by means of positron emission tomography or single photon emission computer tomography. The pharmaceutical may also be used in vivo or ex vivo as an additive in artificial bone substance, in bone cement, or in bone implants.

The invention further relates to the use of a compound V according to the invention in conjunction with a metallic isotope M (such as gadolinium) to produce a pharmaceutical, wherein the metallic isotope M is preferably selected from among the isotopes $^{44}$Sc, $^{47}$Sc, $^{55}$Co, $^{62}$Cu, $^{64}$Cu, $^{67}$Cu, $^{66}$Ga, $^{67}$Ga, $^{68}$Ga, $^{89}$Zr, $^{86}$Y, $^{90}$Y, $^{90}$Nb, $^{99m}$Tc, $^{111}$In, $^{135}$Sm, $^{159}$Gd, $^{149}$Tb, $^{160}$Tb, $^{161}$Tb, $^{165}$Er, $^{166}$Dy, $^{166}$Ho, $^{175}$Yb, $^{177}$Lu, $^{186}$Re, $^{188}$Re, $^{213}$Bi and $^{225}$Ac.

The pharmaceutical according to the invention may be prepared for diagnostic imaging by means of magnetic resonance tomography (nuclear magnetic resonance tomography) or optical imaging. Such a preparation may include the provision of the pharmaceutical in a kit comprising the pharmaceutical as well as usage instructions. [M]DOTA$^{ZOL}$-type pharmaceuticals based on DOTA$^{ZOL}$, as well as derivatives derived from these (for example DOTAM-based derivatives), show an affinity to hydroxyapatite in in vitro assays which largely outperform the affinity of known radiopharmaceuticals containing trivalent metallic radioisotopes M.

Radiopharmaceuticals of the [M]DOTA$^{ZOL}$ type, as well as derivatives derived from these (for example DOTAM-based derivatives), show a significantly better binding to bone in in vivo studies than the known radiopharmaceuticals containing trivalent metallic radioisotopes M. In addition to this, [M]DOTA$^{ZOL}$ and its derivatives (for example, DOTAM-based derivatives) are characterized by an advantageous accumulation ratio of bone-to-blood and bone-to-soft tissue. This is illustrated in FIG. 6, for example.

In comparison to $^{223}$RaCl$_2$ (Xofigo®), radiopharmaceuticals of the [M]DOTA$^{ZOL}$ type, as well as derivatives derived from these (for example, DOTAM-based derivatives) show no accumulation in the intestine and are rapidly excreted via the kidneys.

In comparison to current, particularly successful PSMA tracers (PSMA=Prostate Specific Membrane Antigen), radiopharmaceuticals of the [M]DOTA$^{ZOL}$ type, as well as derivatives derived from these (for example, DOTAM-based derivatives), show a markedly more intensive accumulation at bone metastases in the same patient (factors 2 through 8), simultaneously with significantly reduced accumulation in healthy organs (see example 9). Accordingly, radiopharmaceuticals of the [$^{68}$Ga]DOTA$^{ZOL}$ class (as well as derivatives derived from these—for example, DOTAM-based derivatives such as [$^{68}$Ga]DOTAM$^{ZOL}$) are outperforming the known tracers in imaging diagnostics.

Analogous to this, radiopharmaceuticals of the [$^{77}$Lu]DOTA$^{ZOL}$ class (as well as derivatives derived from these, e.g., DOTAM-based derivatives such as [$^{77}$Lu]DOTAM$^{ZOL}$) are outperforming the known tracers based on trivalent metallic radioisotopes in terms of their therapeutic effect. First clinical studies demonstrate the high selectivity of the compound [$^{177}$Lu]DOTA$^{ZOL}$; see FIG. 5.

Due to their effective and selective accumulation at bone tumors, as well as their therapeutically insignificant residence time in all other organs, radiopharmaceuticals of the [$^{177}$Lu]DOTA$^{ZOL}$ class (as well as derivatives derived from these—for example, DOTAM-based derivatives such as [$^{77}$Lu]DOTAM$^{ZOL}$) open up an alternative to the complicated therapy of bone tumors with $^{223}$Ra. The treatment of bone tumors with $^{223}$Ra has significant disadvantages, such as
(i) limited therapeutic dose and efficiency due to the hematotoxic effect and accumulations of $^{223}$Ra in the intestine, spleen, and liver;
(ii) problematic handling and dose measurement, as well as elaborate safety precautions for dealing with $^{223}$Ra; and
(iii) chemical contamination with $^{225}$Ac, which requires additional cost-intensive purification steps and makes the application of $^{223}$Ra significantly more difficult.

Moreover, $^{77}$Lu-marked DOTA$^{ZOL}$ (as well as derivatives derived from these—for example, DOTAM-based derivatives such as [$^{77}$Lu]DOTAM$^{ZOL}$) lends itself to a markedly more potent treatment of bone metastases after prostate disease than the presently intensively discussed $^{177}$Lu-PSMA derivatives. In comparison to these, a markedly more intensive accumulation—by factors of greater than 2—is to be expected at bone metastases in the same patient, and therefore therapeutically superior dosimetry, simultaneously with significantly reduced accumulation (and therefore less body exposure) in healthy organs.

EXAMPLES

The following examples illustrate embodiments and elements of the present invention, but do not limit the subject matter of the invention to the embodiments and elements illustrated in the examples. If DOTA or its conversion or use is described in the examples, the chelator DOTAM (1,4,7,10-tetrakis(carbamoylmethyl)-1,4,7,10-tetraazacyclododecane) can alternatively be used instead of the chelator DOTA.

Example 1: Synthesis of the Compound DOTA$^{ZOL}$

Instruments and Chemicals Used

ESI-MS: Agilent Technologies 6130 Quadrupole LC/MS Spectrometer or Finnigan MAT-95 Spectrometer. NMR spectrometer: Bruker 600 (Bruker BioSpin AG, Fallanden, Switzerland). DC or Radio DC: Merck Silica on aluminum foil, eluent: 0.1 M citrate pH=4 or acetylacetone:acetone:concentrated HCl (10:10:1). Detector: Canberra Packard Instant Imager. Radio HPLC: Waters-system 1525, column: MultoKrom (CS chromatography) RP18, 5μ, 250×4 mm. Eluent: A (10 mM tetrabutylammonium citrate pH=4.5), B (acetonitrile). Gradient 1 cm$^3$/min (1 mL/min) 70(A):30(B) at 20(A):80(B). Detector: Berthold Technologies (Dresden). $^{68}$Ga/$^{68}$Ge generator: Eckert & Ziegler AG (Berlin). $^{177}$Lu (III) in 0.05 M HCl: itm AG (Munich). μPET: Siemens Focus 120. PET data were processed with Pmod software and OSEM 2D reconstruction. The radioactivity in tissue samples was decay-corrected with an auto gamma counter (WIZARD2, Perkin Elmer, Germany).

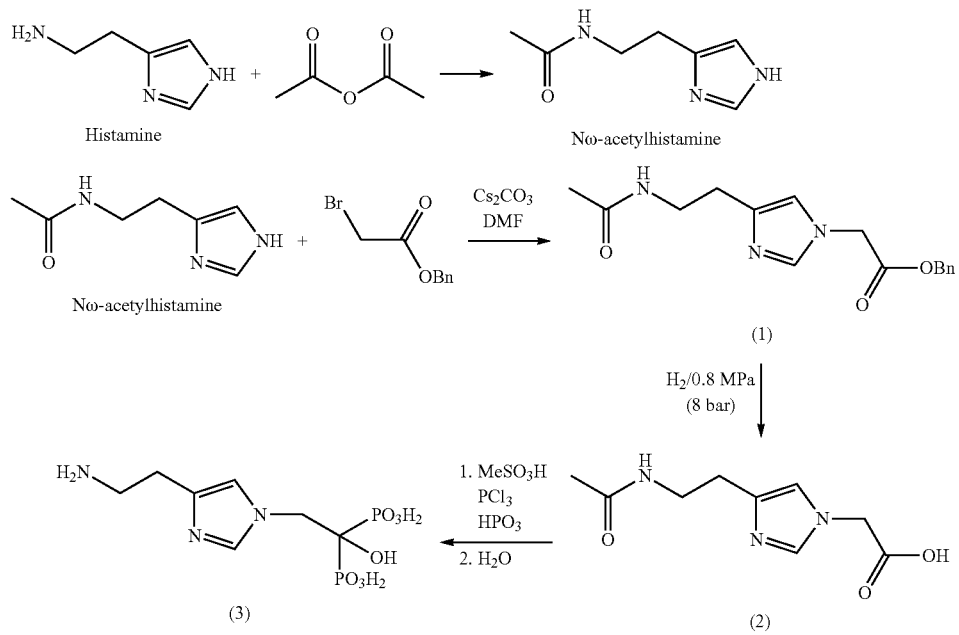

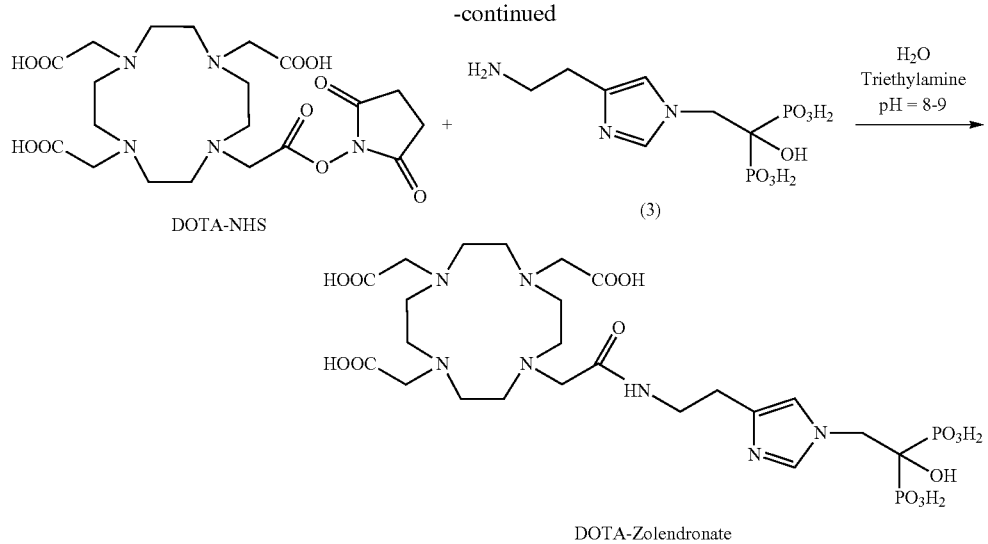

DOTA-Zolendronate

The primary N-ω-acetylhistamine as a starting compound is prepared from histamine with the aid of acetic anhydride. The compound is commercially available (Sigma-Aldrich), but may also be synthesized according to known literature specification from van der Merwe et al., Hoppe-Seyler's Zeitschrift für Physiologische Chemie [Journal of Physiological Chemistry], 177, 1928, 305. DOTA-NHS ester is likewise commercially available, but may also be synthesized according to the following literature specification from Rasaneh et al., Nucl. Med. Biol., 36, 2009, 363-369.

Instead of the chelator DOTA, the chelator DOTAM (1,4,7,10-tetrakis(carbamoylmethyl)-1,4,7,10-tetraazacyclododecane) can alternatively be used that likewise is commercially available or may be synthesized accordingly.
1-(benzyl acetate) 4-(ethylacetamide)-imidazole (1)

Nω-acetylhistamine 1 g (6.53 mmol) is dissolved in 50 mL dry DMF and 4.4 g (13 mmol) cesium carbonate is added. The solution is stirred in an argon atmosphere and ice cooling. 2.2 g (13 mmol) benzyl bromoacetate dissolved in 50 mL dry DMF is slowly added by drops to the suspension. The mixture is stirred for 12 hours before activated carbon is added. The solids are subsequently filtered out, and the solvent is removed in a vacuum. The raw product is recrystallized out of acetyl acetate, and 1.14 g (58%) of 1-(benzyl acetate) 4-(ethylacetamide)-imidazole (1) is obtained as a faintly yellow solid.

$^1$H-NMR (CDCl$_3$, 300 MHz): δ 1.97 (s, 3H, CH$_3$—CO), 2.76 (t, JH=6.3 Hz, 2H, CH$_2$—CH$_2$), 3.53 (q, JH=6.0 Hz, 2H, CH$_2$—CH$_2$), 4.70 (s, 2H, N—CH$_2$—CO), 5.22 (s, 2H, Bn-CH$_2$—CO), 6.53 (bs, 1H, NH), 6.75 (d, JH=1.3 Hz, Imidazole-H), 7.39 (m, 5H, Benzyl), 7.44 (d, JH=1.3 Hz, $^1$H, Imidazole-H).). FD-MS(+): cald 301.14 obsd 302.3 (M+H$^+$), 603.2 (2M+H$^+$).
1-(1-hydroxy-ethane-1,1-bis(phosphonic acid))4-(ethylamine)-imidazole (3)

300 mg (1 mmol) of (1) is dissolved in 20 mL dry methanol and is added Pd/C (10% w). The suspension is stirred for 12 hours under hydrogen atmosphere (0.5 MPa (5 bar)). After the removal of the solvent and the solids, the unprotected acid (2) (208 mg, 98%) was directly converted further. 1 mL methanesulfonic acid and 164 mg (2 eq.) phosphorous acid were added while stirring. The mixture was heated to 75° C., and 300 mg (2.2 eq.) phosphorus trichloride was slowly added by drops in an inert gas atmosphere. After 12 hours, the reaction mixture was cooled to room temperature and added to 2 mL ice water. The solution was subsequently heated for 24 hours with recycling. After the addition of activated carbon, all solids were filtered out and concentrated sodium hydroxide was added by drops to the solution until a white solid began to precipitate. The suspension was stored for 24 hours at 4° C. to complete the precipitation. In the final step, the obtained solid was recrystallized from boiling water, and 88.6 mg (28%) of the aforementioned hydroxybisphosphonate (3) was obtained.

$^1$H-NMR (D$_2$O/NaOD, 300 MHz): δ 2.46 (m, 2H, CH$_2$—CH$_2$), 2.66 (m, 2H, CH$_2$—CH$_2$), 4.28 (m, 2H, N—CH$_2$ phosphonate), 6.89 (s, 1H, Imidazole-H), 7.54 (s, 1H, Imidazole-H). $^{31}$P-NMR (D$_2$O/NaOD, 162.05 MHz): δ 14.4. ESI-MS(+): cald 315.04 obsd 316.05 (M+H$^+$), 338.04 (M+Na$^+$).
DOTA$^{ZOL}$ 15.75 mg (0.05 mmol) (3) is suspended in 1 mL water, and triethylamine (TEA) is added until all solids have dissolved. 38 mg (0.05 mmol) DOTA-NHS ester dissolved in 0.5 mL water is slowly added by drops to the bisphosphonate solution. The reaction mixture is stirred at 50° C. for 24 hours. The pH value is regularly monitored and kept between 8 and 9 via addition of TEA. The raw product is separated from the educts via preparative HPLC (Phenomenex Synergy Hydro-RP 80, 10µ, 250×30 mm, eluent: H$_2$O+0.1% TFA). In a second step, the raw product is additionally purified via solid phase extraction (NH$_2$ phase, Merck LiChroprep NH$_2$). After washing the solid phase with water/methanol/water, the product is eluted from the solid phase via a solution of H$_2$O+2% TFA. After lyophilizing, 5.6 mg (15.7%) of a white solid is obtained.

$^1$H-NMR (D$_2$O/NaOD, 300 MHz): δ 2.42 (m, 2H, CH$_2$—CH$_2$), 2.61 (m, 2H, CH$_2$—CH$_2$), 2.9-3.5 (b, 16H, cyclen-CH$_2$), 3.75 (bs, 8H, —CH$_2$—CO), 4.55 (m, 2H, N—CH$_2$ phosphonate), 7.28 (s, 1H, imidazole-H), 8.54 (s, 1H, imidazole-H). $^{31}$P-NMR (D$_2$O/NaOD, 162.05 MHz): δ 14.3. ESI-MS(+): cald 701.2 obsd 702.5 (M+H$^+$), 351.1 (M+2H$^+$).

Alternatively, the chelator DOTAM (1,4,7,10-tetrakis(carbamoylmethyl)-1,4,7,10-tetraazacyclododecane) can be used instead of the chelator DOTA.

Example 2: Synthesis of [$^{68}$Ga]DOTA$^{ZOL}$ 25 nmol DOTA$^{ZOL}$ are dissolved in 500 μL sodium acetate buffer (0.5 M, pH=4) and added to 400 μL 68Ga(III) solution. The mixture is heated for 15 min at 98° C. The reaction solution is subsequently filtered in a sterile manner. The radiochemical purity is determined—via thin-layer chromatography and HPLC—to be greater than/equal to 95%.

Example 3: Synthesis of [$^{177}$Lu]DOTA$^{ZOL}$ 10 nmol DOTA$^{ZOL}$ per 1 GBq $^{177}$Lu(III) is dissolved in 1 mL sodium acetate buffer (0.1 M, pH=5.0) and added to $^{177}$Lu(III) solution. The mixture is heated for 30 min at 98° C. The reaction solution is subsequently filtered in a sterile manner. The radiochemical purity is determined—via thin-layer chromatography and HPLC—to be greater than/equal to 98%.

Example 4: NHS Coupling of DOTAGA in Slightly Basic Aqueous Solution

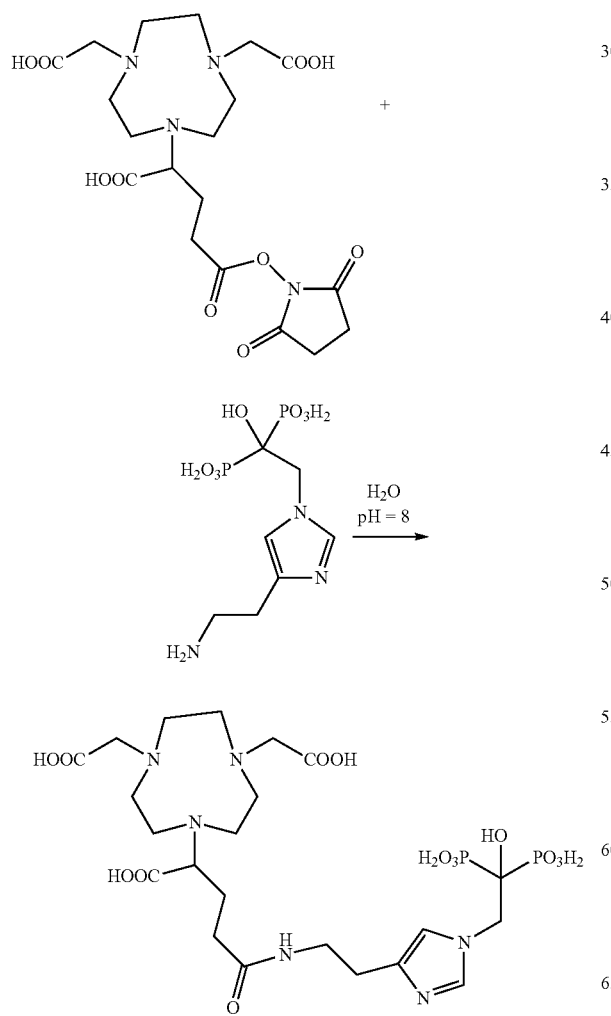

Example 5: NCS Coupling of an HEHA Derivative in Slightly Basic Aqueous Solution

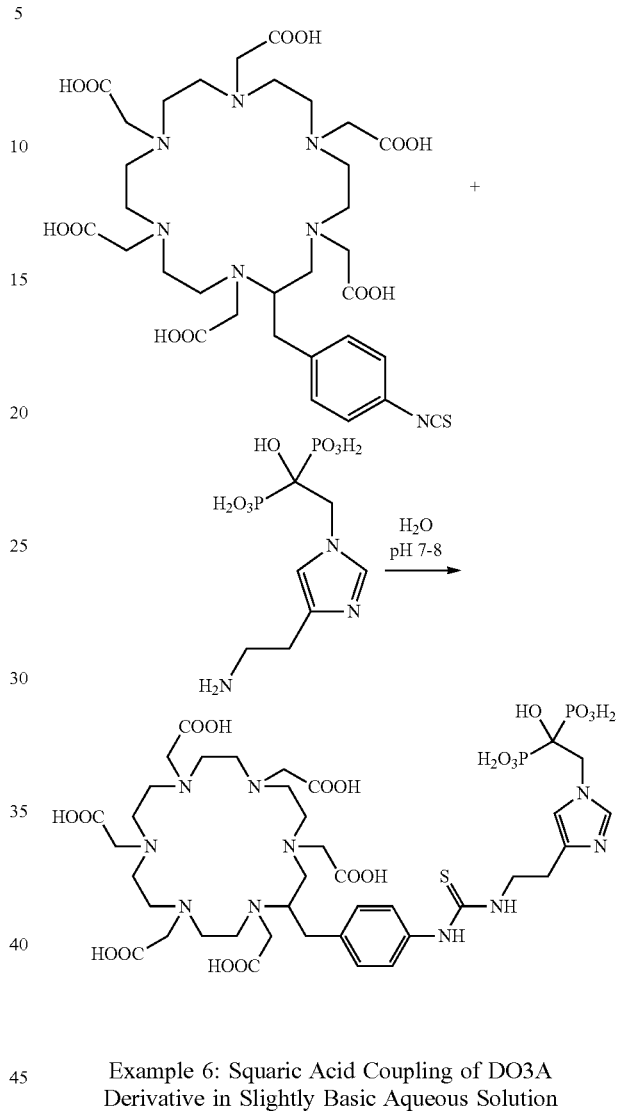

Example 6: Squaric Acid Coupling of DO3A Derivative in Slightly Basic Aqueous Solution

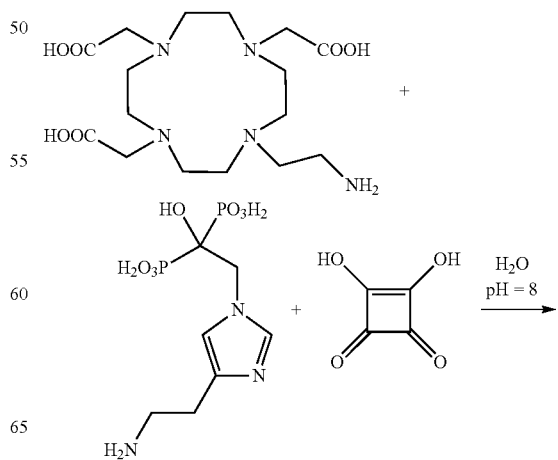

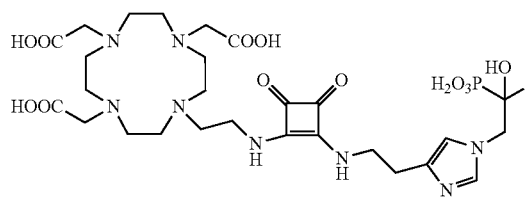

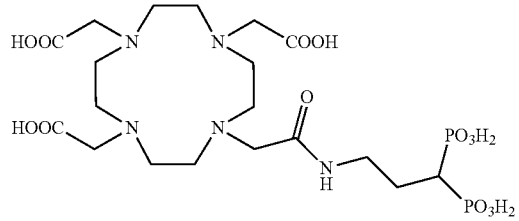

BPAPD (IV)

Example 7: Mannich Reaction of DO3A in Acid Solution

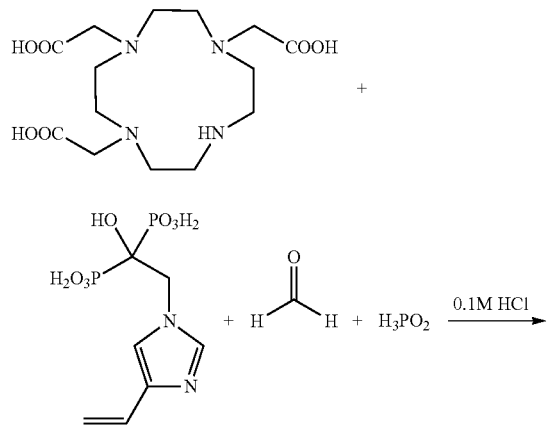

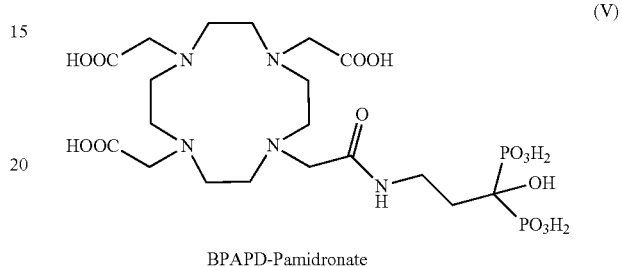

BPAPD-Pamidronate (V)

Measurement results regarding organ distribution of the $^{68}$Ga-marked bisphosphonates described in the preceding are summarized in the following Tables 1 and 2.

TABLE 1

Ex vivo biodistribution of [$^{68}$Ga]BPAPD, [$^{68}$Ga]DOTA$^{PAM}$ and [$^{68}$Ga]DOTA$^{ZOL}$ in Wistar rats after 60 min.

| | SUV | | |
|---|---|---|---|
| Organ | [$^{68}$Ga]BPAPD | [$^{68}$Ga]DOTA$^{PAM}$ | [$^{68}$Ga]DOTA$^{ZOL}$ |
| Lung | 0.43 (0.08) | 0.53 (0.16) | 0.45 (0.11) |
| Liver | 0.37 (0.11) | 0.43 (0.04) | 0.28 (0.03)‡ |
| Spleen | 0.23 (0.08) | 0.31 (0.04) | 0.17 (0.02)‡ |
| Kidneys | 0.56 (0.08) | 0.48 (0.06) | 0.53 (0.04) |
| Muscle | 0.17 (0.02) | 0.09 (0.02) | 0.08 (0.02)† |
| Heart | 0.32 (0.09) | 0.23 (0.02) | 0.14 (0.04)†‡ |
| Blood | 0.86 (0.21) | 0.60 (0.03) | 0.47 (0.19)† |
| Intestine | 0.26 (0.05) | 0.28 (0.12) | 0.14 (0.08) |
| Femur | 3.21 (0.29) | 4.53 (0.17) | 5.40 (0.62)†‡ |

Data presented in SUV (standard deviation) from five animals.
†$P < 0.05$ vs. [$^{68}$Ga]BPAPD;
‡$P < 0.05$ vs. [$^{68}$Ga]DOTA$^{PAM}$.

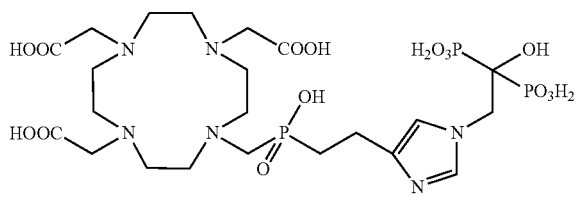

Example 8: In Vivo Experiments in Rats

Under isoflurane anesthesia, 15-18 MBq of the $^{68}$Ga-marked compound or of the $^{177}$Lu-marked compounds, diluted in isotonic saline solution, was applied into the tail vein of healthy Wistar rats (N=5) having a weight between 140 and 220 g. The rats were killed 60 min after injection, organ samples were removed and weighed, and the accumulation of the marked bisphosphonate in the tissue was determined in SUV (standardized uptake value) according to the formula: SUV=(activity per g of tissue)/(injected activity) x body weight.

The known α-Hydroxy-BP BPAPD and a pamidronate-DOTA conjugate (DOTA$^{PAM}$) were chosen as comparison substances. These compounds represent the compounds known in the prior art that are mentioned in the preceding, which have obviously lost their affine amino function due to the derivation with the bifunctional chelator.

TABLE 2

Bone/organ ratios of [$^{68}$Ga]BPAPD, [$^{68}$Ga]DOTA$^{PAM}$ and [$^{68}$Ga]DOTA$^{ZOL}$ in Wistar rats after 60 min.

| | Bone-to-organ ratios | | |
|---|---|---|---|
| | [$^{68}$Ga]BPAPD | [$^{68}$Ga]DOTA$^{PAM}$ | [$^{68}$Ga]DOTA$^{ZOL}$ |
| Lung | 7.47 | 8.61 | 12.06 |
| Liver | 8.68 | 10.02 | 19.21 |
| Spleen | 13.96 | 14.51 | 31.71 |
| Kidneys | 5.73 | 9.44 | 10.22 |
| Muscle | 18.88 | 47.96 | 65.96 |
| Heart | 10.03 | 19.49 | 37.97 |
| Blood | 3.73 | 7.61 | 11.47 |
| Intestine | 12.35 | 16.11 | 38.67 |

TABLE 3

Pharmacological parameters (2-Compartment Model) from the in vivo μPET experiments with [$^{68}$Ga]BPAPD, [$^{68}$Ga]DOTA$^{PAM}$ and [$^{68}$Ga]DOTA$^{ZOL}$ in Wistar rats.

| Elimination half-life | [$^{68}$Ga]BPAPD | [$^{68}$Ga]DOTA$^{PAM}$ | [$^{68}$Ga]DOTA$^{ZOL}$ |
|---|---|---|---|
| $t_{1/2}(\alpha)$ | 5 min | 4.5 min | 5 min |
| $t_{1/2}(\beta)$ | 4 h | 4.5 h | 2.3 h |

Alternatively, the chelator DOTAM (1,4,7,10-tetrakis(carbamoylmethyl)-1,4,7,10-tetraazacyclododecane) can be used instead of the chelator DOTA.

Example 9: Accumulation at Bone Metastases

In comparison to current, particularly successful PSMA tracers (PSMA=Prostate Specific Membrane Antigen), radiopharmaceuticals of the [M]DOTA$^{ZOL}$ type, as well as derivatives derived from these (for example, DOTAM-based derivatives), show a markedly more intensive accumulation at bone metastases in the same patient (factors 2 through 8) simultaneously with significantly reduced accumulation in healthy organs (see example 9). The table shows the measured uptake (as SUV max values) of [$^{68}$Ga]DOTA$^{ZOL}$ and [$^{68}$Ga]HBED-PSMA$^{CC}$ in direct comparison in a patient with prostate carcinoma and bone metastases.

TABLE 4

SUV max. values of [$^{68}$Ga]DOTA$^{ZOL}$ and [$^{68}$Ga]HBED-PSMA$^{CC}$ in direct comparison in a patient with prostate carcinoma and bone metastases.

|  | Organ | [$^{68}$Ga]DOTA$^{ZOL}$ PET/CT Day n SUV max | [$^{68}$Ga]HBED-PSMA$^{CC}$ PET/CT Day n + 2 (meaning 2 days later) SUV max |
|---|---|---|---|
| Bone lesions | C4 vertebral body and hip pedicle | 12.38 | 7.97 |
|  | 8th right rear rib | 7.99 | 7.12 |
|  | T9 vertebral body | 17.08 | 7.60 |
|  | T11 vertebral body | 32.29 | 12.98 |
|  | L2 vertebral body | 68.92 | 8.85 |
|  | L3 vertebral body | 62.96 | 9.46 |
|  | L4 vertebral body | 34.51 | 10.98 |
|  | L5 vertebral body | 21.94 | 19.99 |
|  | Sacrum | 17.98 | 14.96 |
|  | Right ischium | 32.55 | 14.96 |
|  | Left bones, upper ischium, and pubic bone | 62.32 | 8.99 |
|  | Right acetabulum | 25.39 | 11.71 |
| Soft tissue | Right parotid gland | 1.22 | 5.80 |
|  | Left parotid gland | 1.46 | 6.48 |
|  | Liver | 2.85 | 6.48 |
|  | Spleen | 4.50 | 3.27 |
|  | Right kidney | 9.34 | 22.72 |
|  | Left kidney | 4.12 | 5.75 |
|  | Bladder | 15.53 | 22.23 |

BRIEF DESCRIPTION OF FIGURES

Accompanying Figures illustrate embodiments and elements of the present invention, but do not limit the subject matter of the invention to the embodiments and elements illustrated in the Figures. If DOTA or its conversion or use is described in the Figures, the chelator DOTAM (1,4,7,10-tetrakis(carbamoylmethyl)-1,4,7,10-tetraazacyclododecane) can alternatively be used instead of the chelator DOTA.

Figure 1:
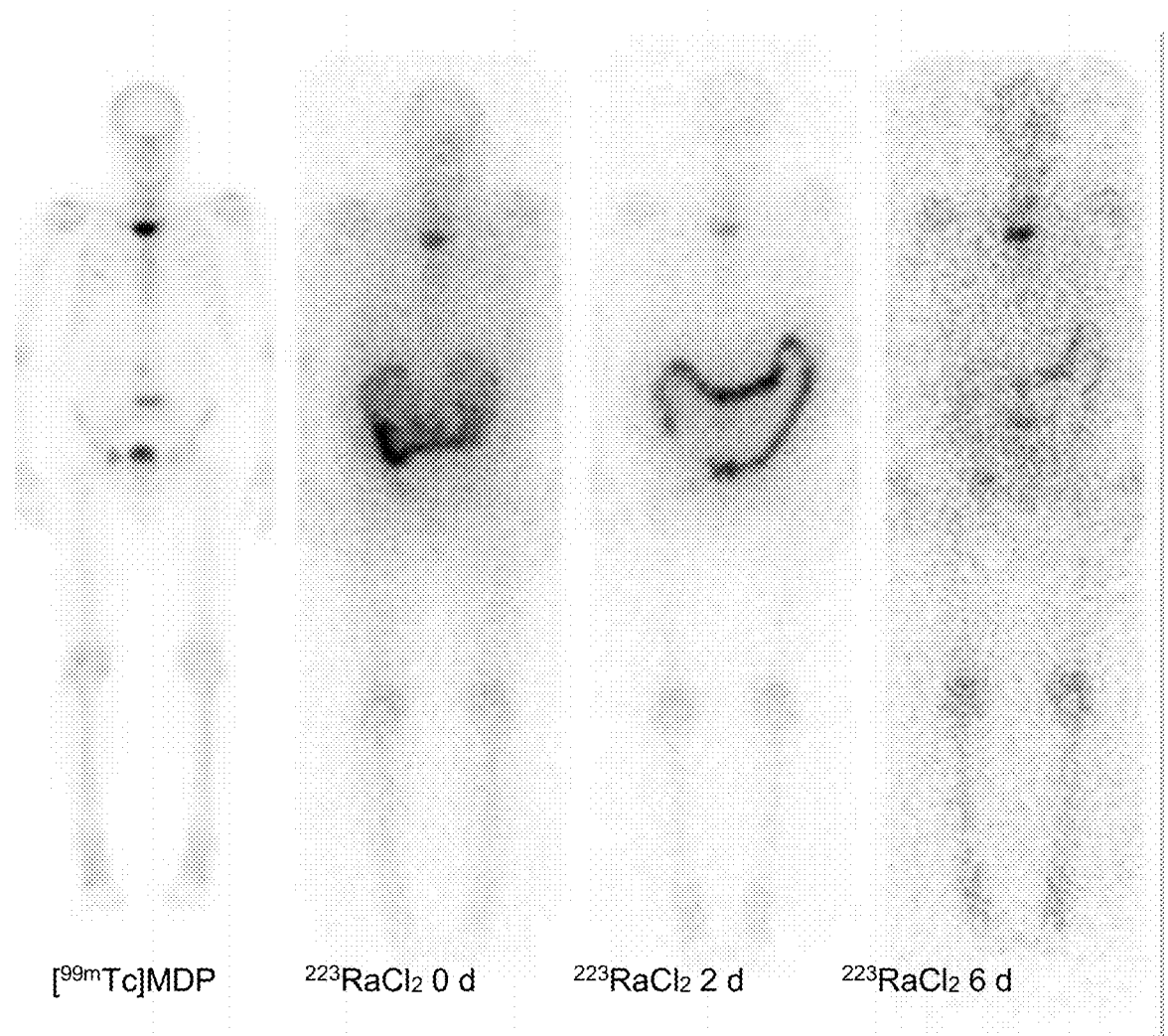
FIG. 1: Comparison of [$^{99m}$Tc]MDP and $^{223}$RaCl$_2$ on day 1, 2, and day 6 after the injection, from O. Sartor, P. Hoskin, Ø. S. Bruland, Targeted radio-nuclide therapy of skeletal metastases, Cancer Treatment Reviews, 2013; 39: 18-26.
Figure 2:
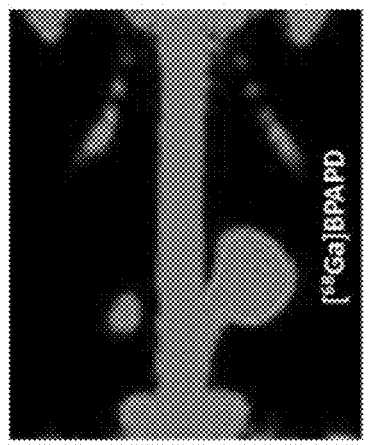
FIG. 2: μPET exposures of various $^{68}$Ga(III)-marked macrocyclic bisphosphonates in healthy Wistar rats after 60 min, in Maximum Intensity Projection operating mode.
Figure 2:
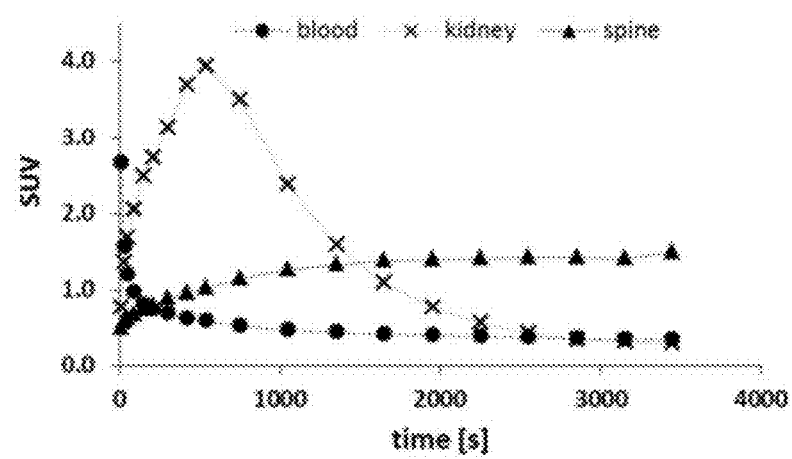
Figure 2:
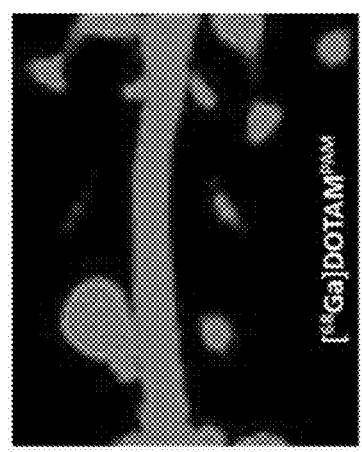
Figure 2:
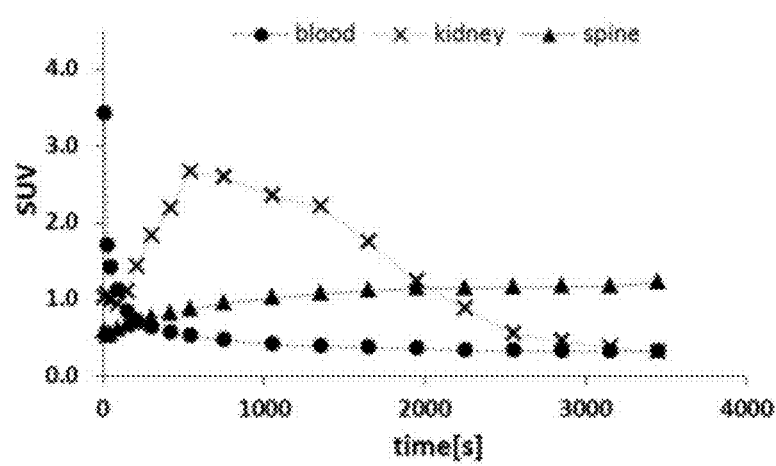
Figure 2:
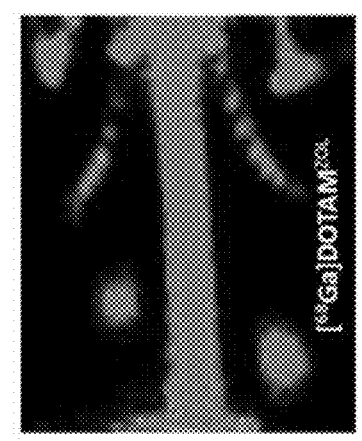
Figure 2:
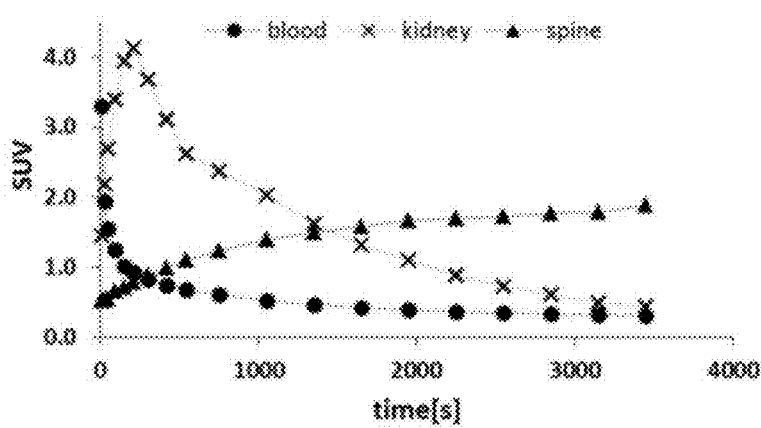
Figure 3:
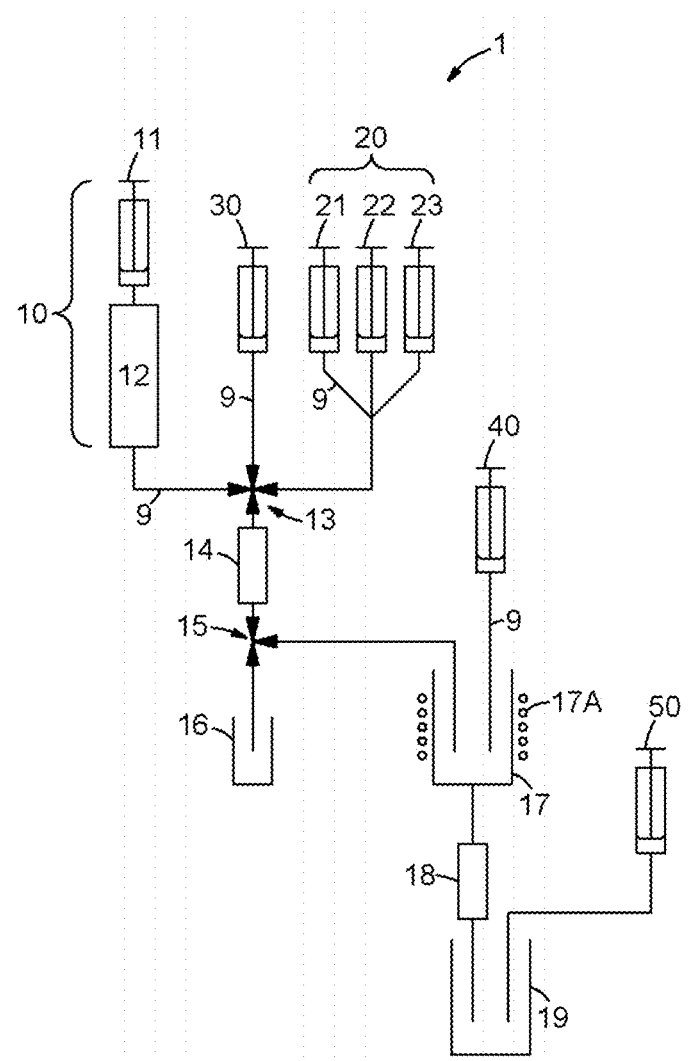
FIG. 3 schematically shows a first device 1 for producing a radiopharmaceutical made up of the compound V, as described in detail above.
Figure 4:
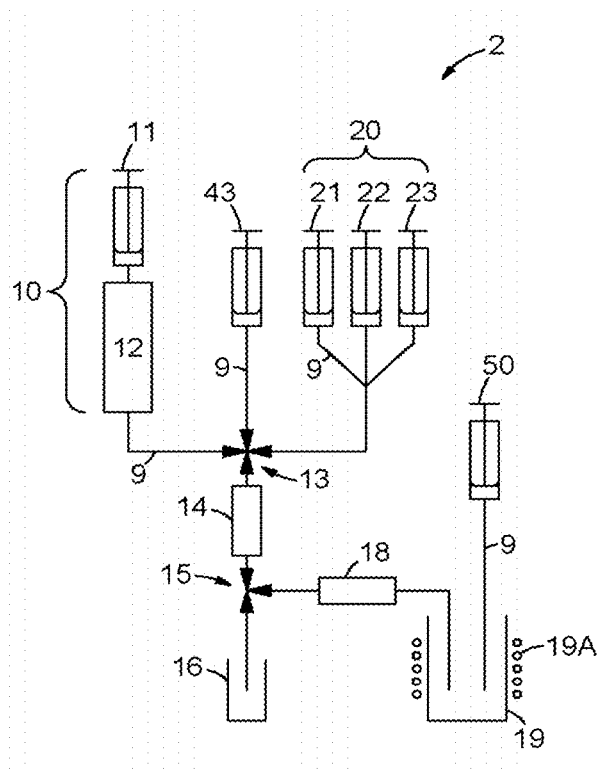
FIG. 4 schematically shows a second device 2 for producing a radiopharmaceutical made up of the compound V according to the invention and a metallic radioisotope M, as described in detail above.
Figure 5:
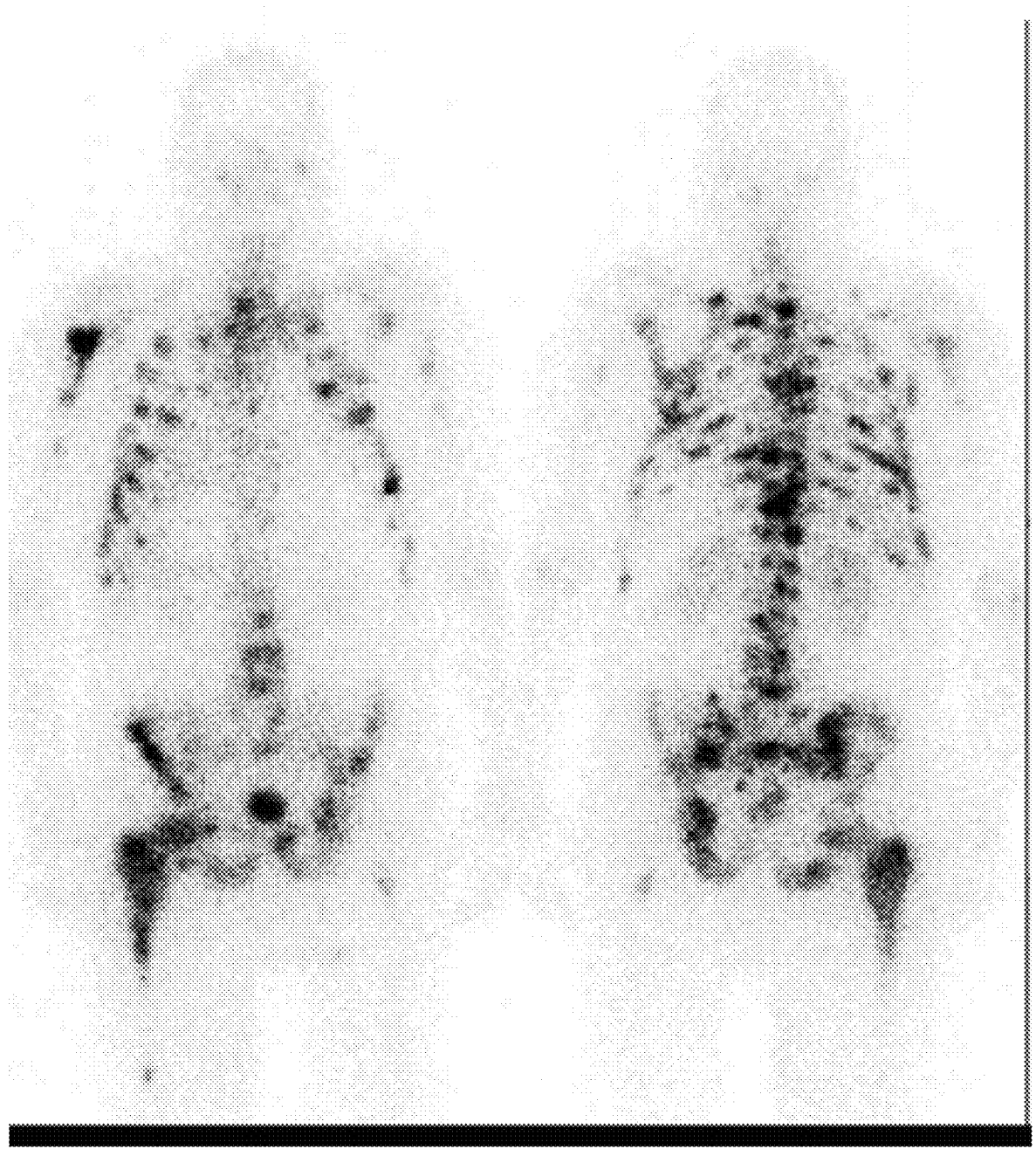
FIG. 5: Distribution of [$^{177}$Lu]DOTA$^{ZOL}$ in a patient with disseminated bone metastases: [$^{177}$Lu]DOTA$^{ZOL}$ scintigraphy on a patient with prostate carcinoma 6 hours after injection. In a first therapeutic applications [sic], within two months, the PSA value (which represents an important marker in monitoring the progress of the prostate carcinoma) could be lowered from 478 ng/mL initially to 88 ng/mL after only one treatment with 5.5 GBq [$^{177}$Lu]DOTA$^{ZOL}$. $^{177}$Lu-DOTAM$^{ZOL}$ may be used equivalently.
Figure 6:
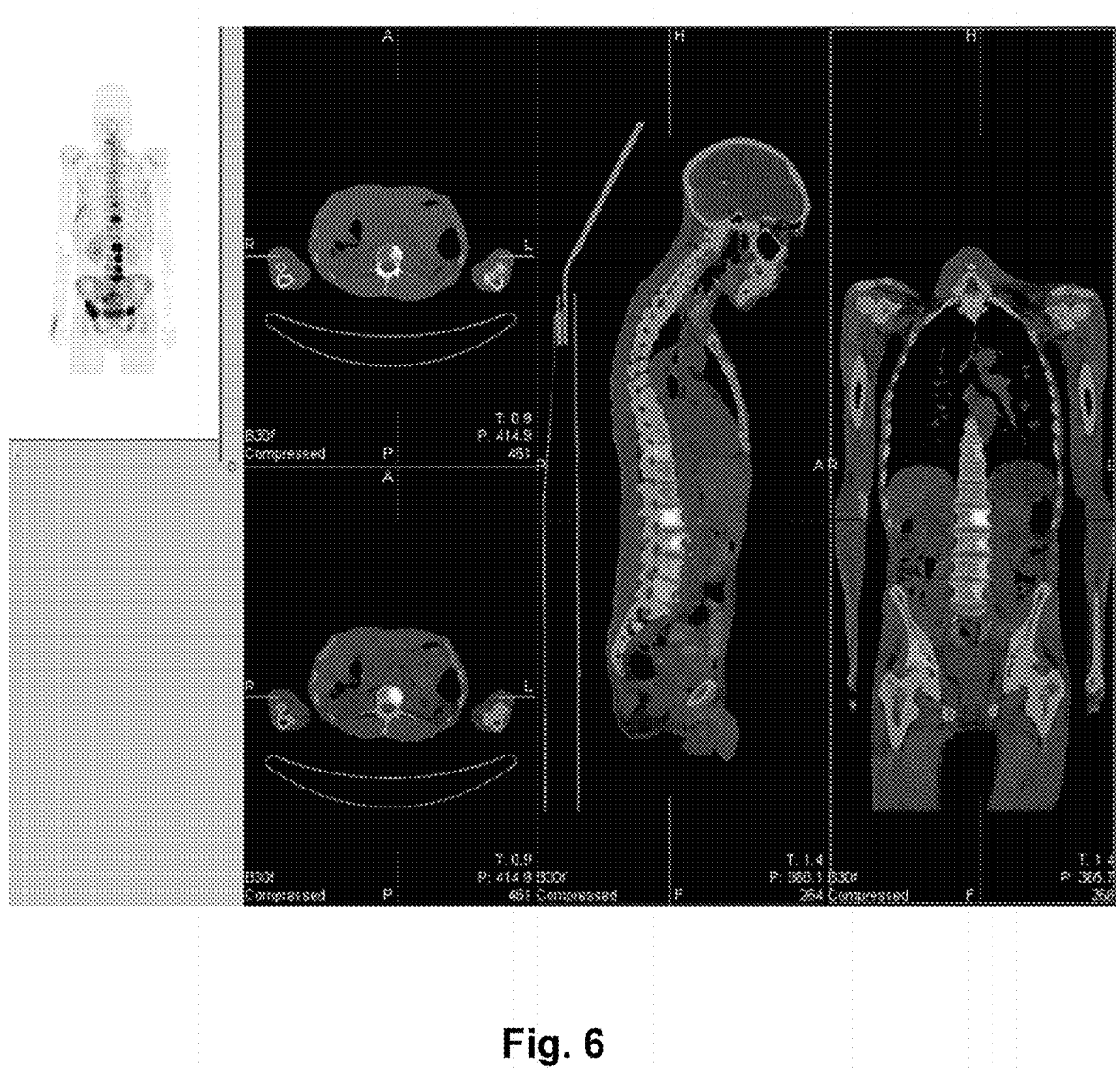
FIG. 6: PET/CT scan of a prostate carcinoma patient with bone metastases, examined with $^{68}$Ga-DOTA$^{ZOL}$. $^{68}$Ga-DOTAM$^{ZOL}$ may be used equivalently.

The invention claimed is:

1. Compound V for complexing metallic isotopes, comprising a chelator X and one or more targeting vectors conjugated with the chelator X, said targeting vectors having the structure -L$_1$-R$_1$-L$_2$-R$_2$-L$_3$-R$_3$, wherein L$_1$ is selected from the group consisting of: amide, phosphinate, alkyl, triazole, thiourea, ethylene, maleimide, —(CH$_2$)$_k$— and —(CH$_2$CH$_2$O)$_k$—, where k is 1, 2, 3, 4, 5, 6, 7, 8, 9, or 10, L$_2$ is selected from —(CH$_2$)$_m$— and —(CH$_2$CH$_2$O)$_m$—, where m is 1, 2, 3, 4, 5, 6, 7, 8, 9, or 10, and L$_3$ is selected from —(CH$_2$)$_n$— and —(CH$_2$CH$_2$O)$_n$—, where n is 1, 2, 3, 4, 5, 6, 7, 8, 9, or 10, characterized in that

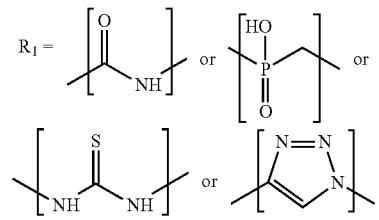

R$_2$ is selected from the group consisting of: a substituent group of a:
furan, azole, oxazole, thiophen, thiazole, azine, oxazine, thiazine, naphthalene, quinoline, chromene, thiochromene, pyrrole, pyridine, pyrimidine, oxadiazole or thiadiazole; and

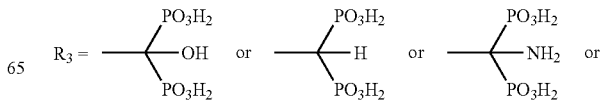

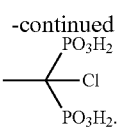

2. Compound V according to claim 1, characterized in that the chelator X is selected from the group consisting of: EDTA (ethylenediamine-tetraacetate), EDTMP (diethylenetriamine penta(methylene phosphonic acid)), DTPA (diethylenetriamine pentaacetic acid) and its derivatives, DOTA (1,4,7,10-tetraazacyclododecane-1,4,7,10-tetraacetic acid), DOTAGA (dodeca-1-glutaric acid-1,4,7,10-tetraamine-triacetic acid), DOTAM (1,4,7,10-tetrakis(carbamoylmethyl)-1,4,7,10-tetraazacyclododecane) and other DOTA derivatives, TRITA (trideca-1,4,7,10-tetraamine tetraacetic acid), TETA (tetradeca-1,4,8,11-tetraamine-tetraacetic acid) and its derivatives, NOTA (nona-1,4,7-triamine-triacetic acid) and its derivatives,NOTAGA (1,4,7-triazacyclononane, 1-glutaric acid,4,7-acetic acid), NOPO (1,4,7-triazacyclononane-1,4-bis[methylene(hydroxymethyl)hypophosphorous acid]-7-[methylene(2-carboxyethyl)hypophosphorous acid]) and its derivatives, PEPA (pentadeca-1,4,7,10,13-pentaamine pentaacetic acid) and its derivatives, HEHA (hexadeca-1,4,7,10,13,16-hexaamine hexaacetic acid) and its derivatives, HBED (hydroxybenzyl-ethylenediamine) and its derivatives, DEDPA and its derivatives, H₂DEDPA (1,2-[{6-(carboxylate-)pyridine-2-yl}methylamine]ethane), DFO (deferoxamine) and its derivatives, Deferiprone, CP256 (4-acetylamino-4-{2-[(3-hydroxy-1,6-dimethyl-4-oxo-1,4-dihydro-pyridine-2-ylmethyl)-carbamoyl]-ethyl}-heptane diacid bis-[(3-hydroxy-1,6-dimethyl-4-oxo-1,4-dihydro-pyridine-2-ylmethyl)-amide]) and its derivatives, YM103; TRAP (triazacyclononane-hypophosphorous acid) and its derivatives, TEAP (tetraazycyclodecane -hypophosphorous acid) and its derivatives, AAZTA (6-amino-6-methylperhydro-1,4-diazepine -N,N,N',N'-tetraacetic acid) and derivatives such as DATA; SarAr (1-N-(4-aminobenzyl)-3,6,10,13,16,19-hexaazabicyclo[6.6.6]-eicosane-1,8-diamine) and salts thereof.

3. Compound V according to claim 1 characterized in that the compound V has a structure according to Formula I

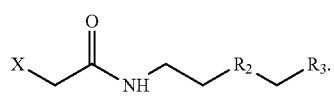

(I)

4. Compound V according to claim 1, characterized in that the compound has a structure according to Formula II

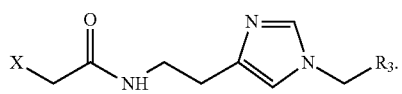

(II)

5. A pharmaceutical composition comprising the compound V according to claim 1, and a metallic isotope M complexed with the compound V.

6. The pharmaceutical composition according to claim 5, characterized in that the metallic isotope M is selected from the group consisting of: $^{44}$Sc, $^{47}$Sc, $^{55}$Co, $^{62}$Cu, $^{64}$Cu, $^{67}$Cu, $^{66}$Ga, $^{67}$Ga, $^{68}$Ga, $^{89}$Zr, $^{86}$Y, $^{90}$Y, $^{90}$Nb, $^{99m}$Tc, $^{111}$In, $^{135}$Sm, $^{159}$Gd, $^{149}$Tb, $^{160}$Tb, $^{161}$Tb, $^{165}$Er, $^{166}$Dy, $^{166}$Ho, $^{175}$Yb, $^{177}$Lu, $^{186}$Re, $^{168}$Re, $^{213}$Bi and $^{225}$Ac.

7. A method for producing a pharmaceutical composition according to claim 5, comprising the following steps:
(a) providing a solution S containing the compound V;
(b) providing a metallic isotope M; and
(c) ligating the metallic isotope M with the compound V to form a complex MV of the metallic isotope M with the compound V in a solution F.

8. The method according to claim 7, characterized in that, in step (b), the metallic isotope M is provided in a solution.

9. The method according to claim 7, characterized in that, in step (b), a radionuclide generator with a mother nuclide and a metallic isotope M formed via decay of the mother nuclide is provided, and, in step (c), the metallic isotope M is separated from the mother nuclide with the solution S.

10. A method of medical treatment or medical imaging comprising administration of a pharmaceutical composition according to claim 5 to a subject.

11. The method according to claim 10 wherein the treatment is treatment of a bone disease.

12. The method according to claim 10 wherein the treatment is treatment of a bone tumors.

13. The method according to claim 12, wherein the treatment is treatment of a diseases of unmanifested bone metastases.

14. The method according to claim 13, wherein the treatment comprises accumulation of the pharmaceutical composition in a tumor cell in order to inhibit farnesyl pyrophosphate synthesis (FPPS).

15. The method according to claim 10, wherein the medical imaging comprises positron emission tomography, single photon emission computer tomography, magnetic resonance tomography (nuclear magnetic resonance tomography) or optical imaging.

16. The pharmaceutical composition according to claim 5 further comprising an artificial bone substance, a bone cement, or a bone implants.

17. Compound V according to claim 1, wherein R₂ is an azole, oxazole, oxadiazole, thiazole or thiadizaole selected from the group consisting of:

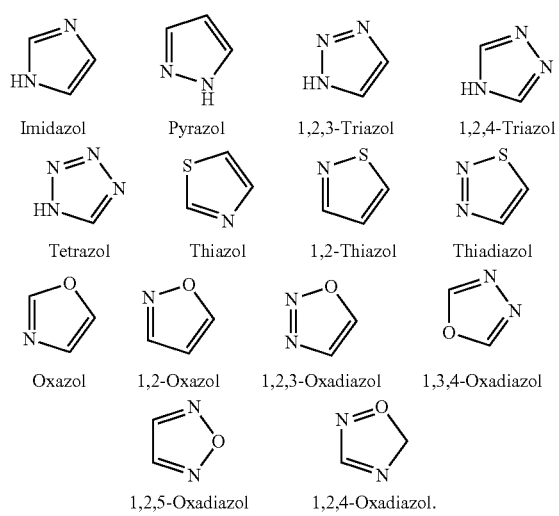

18. Compound V according to claim 1, selected from the group consisting of:

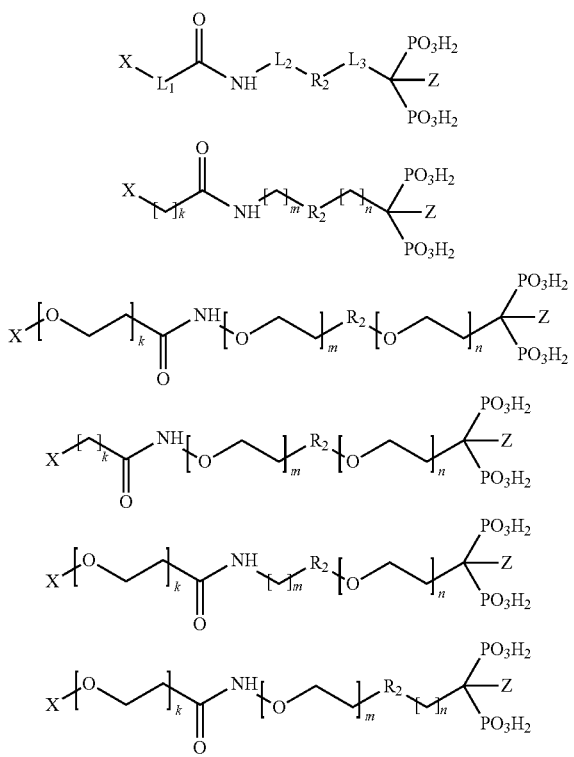
where k is 1, 2, 3, 4, 5, 6, 7, 8, 9 or 10; m is 1, 2, 3, 4, 5, 6, 7, 8, 9 or 10; n is 1,2,3,4,5,6,7,8, 9 or 10; and Z is OH, H, $NH_2$ or Cl.
19. Compound V according to claim 1, having the structure:
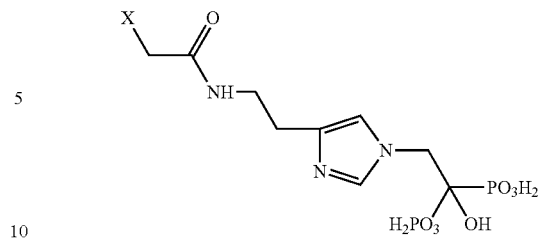
where X is DOTA, DOTAM DOTAGA.
20. Compound V according to claim 1, wherein $R_2$ is an azine, oxazine, or thiazine selected from the group consisting of:
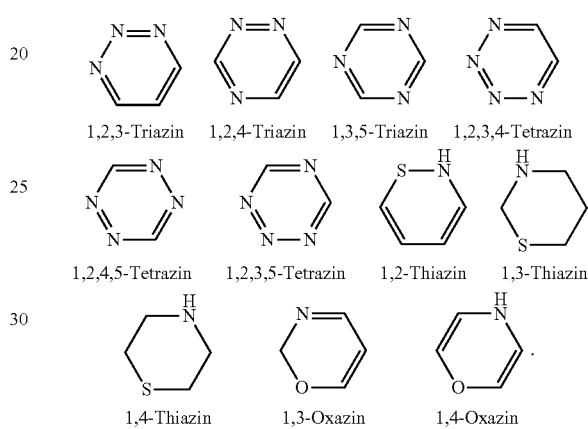
* * * * *